US012611238B2

(12) United States Patent
Berlet et al.

(10) Patent No.: US 12,611,238 B2
(45) Date of Patent: Apr. 28, 2026

(54) WEDGE OSTEOTOMY DEVICES, SYSTEMS, AND METHODS FOR TREATING MID-FOOT DISORDERS

(71) Applicant: Apex Orthopedics, LLC, Aurora, CO (US)

(72) Inventors: Gregory C. Berlet, Westerville, OH (US); Stephen A. Brigido, Bethlehem, PA (US); Murray J. Penner, Vancouver (CA)

(73) Assignee: Innovative Midfoot Solutions, Inc., Aurora, CO (US)

( * ) Notice: Subject to any disclaimer, the term of this patent is extended or adjusted under 35 U.S.C. 154(b) by 286 days.

(21) Appl. No.: 18/459,027

(22) Filed: Aug. 30, 2023

(65) Prior Publication Data

US 2024/0065740 A1     Feb. 29, 2024

Related U.S. Application Data

(60) Provisional application No. 63/402,879, filed on Aug. 31, 2022.

(51) Int. Cl.
*A61B 17/80* (2006.01)
*A61B 17/00* (2006.01)

(52) U.S. Cl.
CPC *A61B 17/8095* (2013.01); *A61B 2017/00004* (2013.01); *A61B 2017/00526* (2013.01); *A61B 2017/00831* (2013.01)

(58) Field of Classification Search
CPC .................. A61B 17/8095; A61B 2017/00004
See application file for complete search history.

(56) References Cited

U.S. PATENT DOCUMENTS

| | | | | | |
|---|---|---|---|---|---|
| 5,620,448 | A | * | 4/1997 | Puddu | A61B 17/88 |
| | | | | | 606/83 |
| 6,008,433 | A | * | 12/1999 | Stone | A61B 17/8095 |
| | | | | | 623/20.14 |
| 10,857,268 | B2 | * | 12/2020 | Robinson | A61M 1/98 |
| 2002/0082699 | A1 | * | 6/2002 | Ward | A61L 27/16 |
| | | | | | 623/23.51 |
| 2013/0331946 | A1 | | 12/2013 | Shohat | |
| 2016/0235455 | A1 | * | 8/2016 | Wahl | A61F 2/42 |

OTHER PUBLICATIONS

International Searching Authority. International Search Report. International Application No. PCT/US2023/073231. Dated Feb. 15, 2024.
International Searching Authority. Written Opinion of the International Searching Authority. International. Application No. PCT/US2023/073231. Dated Feb. 14, 2024.

* cited by examiner

Primary Examiner — Christian A Sevilla
(74) Attorney, Agent, or Firm — Rosenbaum IP, P.C.; David G. Rosenbaum

(57)     ABSTRACT

Devices, systems and methods for surgical treatment of mid-foot disorders such as osteoarthritis, spacing disorders, or alignment disorders, including mid-foot arthroplasty devices and systems for the $2^{nd}$ and $3^{rd}$ tarsometatarsal (TMT) joint, implants for post-osteotomy spacing and realignment, arthroplasty articular implants, dowel grafts for TMT arthrodesis or fusion, dowel grafts for navicular cuneiform (NC) arthrodesis, dowel grafts for intercuneiform arthrodesis, and/or locking dowels for joint fusion.

14 Claims, 18 Drawing Sheets

BIOFOAM
Wedge System

CLAW II
POLYAXIAL COMPRESSION
PLATING SYSTEM

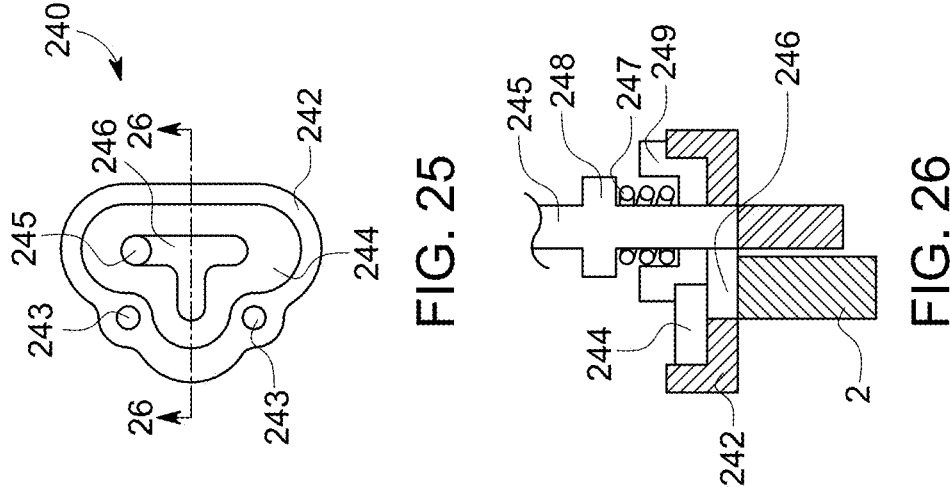
FIG. 25
FIG. 26
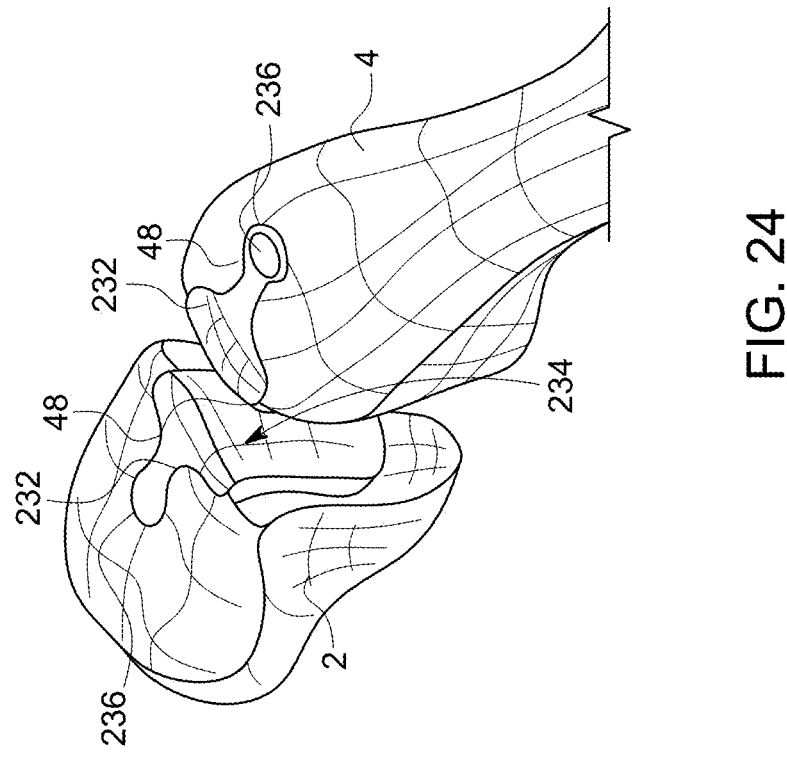
FIG. 24

WEDGE OSTEOTOMY DEVICES, SYSTEMS, AND METHODS FOR TREATING MID-FOOT DISORDERS

CROSS-REFERENCE TO RELATED APPLICATIONS

This applications is related to and claims priority to U.S. Provisional Patent Application Ser. No. 63/402,879, filed Aug. 31, 2022.

BACKGROUND OF THE INVENTION

The present disclosure pertains generally to instrumentation, devices, and methods for surgical treatment of orthopedic mid-foot disorders such as osteoarthritis, spacing disorders, or alignment disorders. More specifically, the present disclosure pertains to: i) tarsometatarsal (TMT) joint arthroplasty devices and methods; ii) a midfoot joint finder and method; iii) adjustable osteotomy wedge system and devices; iv) a wedge osteotomy arcuate distractor; and v) dowel implants and non-circular conical dowel implants for orthopedic arthrodesis procedures. The devices, instrumentation, and methods of the present disclosure also have relevance and pertains to all transverse or vertically-oriented joint fusions, including, without limitation in the hand, wrist, foot, and/or ankle.

Currently, most flatfoot reconstruction entails correction of the hindfoot and the medial column of the foot orthopedic architecture is typically viewed as irrelevant or too difficult. This has led to scant effort to create power, yet readily performed and reliable procedures involving medial column or mid-foot correction procedures. Plantarflexion navicular-cuneiform joint fusion, along with tendon transfer, and/or Cotton osteotomy and/or plantarflexion tarsometatarsal joint fusion are all components of medial column deformity correction.

SUMMARY OF THE INVENTION

It is an object of the present disclosure to provide instrumentation, devices, and methods for surgical treatment of orthopedic mid-foot disorders.

It is another object of the present disclosure to provide instrumentation, devices, and methods for mid-foot joint fusion.

It is another further object of the present disclosure to instrumentation, devices, and methods for mid-foot joint arthrodesis.

It is still another object of the present disclosure to provide instrumentation, devices, and methods for fusion or arthrodesis of the tarsometatarsal joints, navicular cuneiform joints, the metartasocuneiform joints, the talon-navicular joints, the intercuneiform joints, the subtalar joint, the calcaneocuboid joint, and/or the metartasalphalangeal joints of the foot.

It is still another object of the present disclosure to provide instrumentation, devices, and methods for fusion or arthrodesis of the hand or wrist joints.

It is another further object of the present disclosure to provide implants for post-osteotomy spacing and realignment.

It is yet another further object of the present disclosure to provide non-circular dowel grafts for mid-foot joint fusion.

It is yet another object of the present disclosure to provide an arcuate distractor for wedge osteotomy of bones, including, without limitation, the medial cuneiform or calcaneus bones.

It is still a further object of the present disclosure to provide an adjustable osteotomy wedge system for orthopedic alignment of bones.

It is yet a further object of the present disclosure to provide a method of TMT joint arthroplasty.

It is still another further object of the present disclosure to provide a joint finder instrument useful in fusion and arthroplasty procedures, including those of the midfoot bones.

BRIEF DESCRIPTION OF THE DRAWINGS

FIG. 24 is a perspective view of a slot insert implanted in a cuneiform bone of a tarsometatarsal joint.

FIG. 25 is a top elevational view of a drill guide for forming a recess in a cuneiform bone at a tarsometatarsal joint to accommodate the slot insert of the present invention.

FIG. 26 is a cross-sectional view taken along line 26-26 of FIG. 25 illustrating engagement with a drill burr.

DETAILED DESCRIPTION OF THE PREFERRED EMBODIMENTS

Figure 1:
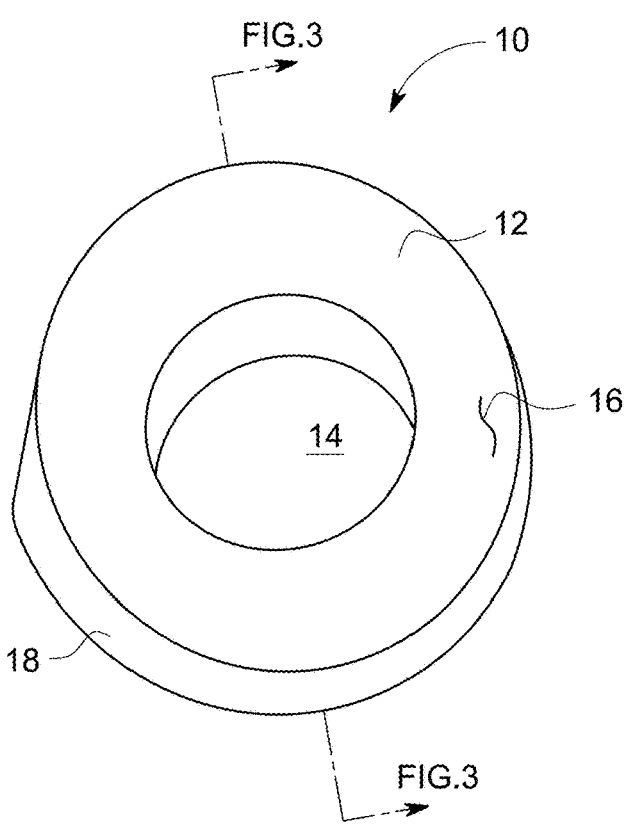
FIG. 1 is a perspective view of a biocompatible wedge implant for post-osteotomy spacing and realignment in accordance with the present disclosure.
Figure 2:
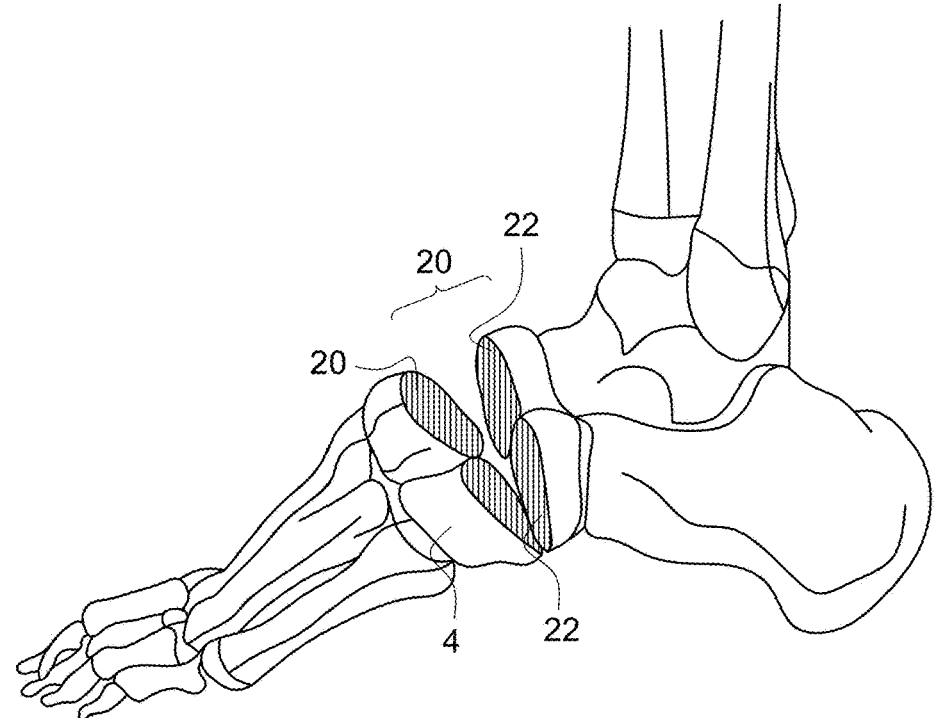
FIG. 2 is a perspective view of the biocompatible wedge implant shown implanted in the mid-foot architecture.

For purposes of clarity, the following terms used in this patent application will have the following meanings:

The terminology used herein is for the purpose of describ- ing example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated fea- tures, integers, steps, operations, elements, and/or compo- nents, but do not preclude the presence or addition of one or more other features, integers, steps, operations, elements, components, and/or groups thereof. The method steps, pro- cesses, and operations described herein are not to be con- strued as necessarily requiring their performance in the order discussed or illustrated, unless specifically identified as an order of performance. It is also to be understood that additional or alternative steps may be employed.

When an element or layer is referred to as being "on," "engaged," "connected," or "coupled" to or with another element, it may be directly on, engaged, connected or coupled to the other element or layer, or intervening ele- ments or layers may be present. In contrast, when an element is referred to as being "directly on," "directly engaged to," "directly connected to," or "directly coupled to" or with another element or layer, there may be no intervening elements or layers present. Other words used to describe the relationship between elements should be interpreted in a like fashion (e.g., "between" versus "directly between," "adja- cent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

"Substantially" is intended to mean a quantity, property, or value that is present to a great or significant extent and less than, more than or equal to total. For example, "substantially vertical" may be less than, greater than, or equal to completely vertical.

"About" is intended to mean a quantity, property, or value that is present at ±10%. Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges.

Recitation of ranges of values herein are merely intended to serve as a shorthand method of referring individually to each separate value falling within the recited range, unless otherwise indicated herein, and each separate value is incorporated into the specification as if it were individually recited herein.

References to "embodiment" or "variant", e.g., "one embodiment," "an embodiment," "example embodiment," "various embodiments," etc., may indicate that the embodiment(s) or variant(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment or variant, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The term "material" is intended to refer to encompass biocompatible materials, including metals, ceramics, polymers, composites, and combinations or hybrids thereof.

As used in this application the term "layer" is intended to mean a substantially uniform material limited by interfaces between it and adjacent other layers, substrate, or environment.

The terms "circumferential" or "circumferential axis" is intended to refer to the radial direction of a tubular, cylindrical or annular material or to the Y-axis of a polygonal material.

The terms "longitudinal," "longitudinal axis," or "tube axis" are intended to refer to an elongate aspect or axis of a material or to the X-axis of the material.

The term "medial" is intended to denote a position towards the midline of the body.

The term "lateral" is intended to mean a position away from the midline of the body.

The term "plantar" is intended to refer to a position toward the sole of the foot.

The term "dorsal" is intended to refer to a position away from the sole of the foot.

The term "mid-foot" is intended to mean the medial column section of the human foot between the hindfoot and forefoot and includes five of the seven tarsal bones, i.e., navicular, cuboid, and three cuneiform bones.

The term "hindfoot" is intended to mean the posterior section of the human foot comprising the region of the talus and calcaneus bones.

The term "forefoot" is intended to mean the anterior section of the human foot comprising the metatarsal and phalangeal bones.

The terms "tarsometatarsal" or "TMT" are intended to relate to the articulations between the tarsal and metatarsal bones of the foot and the ligaments in relation thereto.

The terms "metartasocuneiform" or "MC" are intended to relate to the joint or articulations between the metatarsal and cuneiform bones of the human foot and the ligaments in relation thereto.

The terms "navicular cuneiform" or "NC" are intended to refer to the joint or articulations in the human mid-foot consisting of the tarsal, navicular, and the medial, middle, and lateral cuneiform bones.

The terms "talon-navicular" or "TN" are intended to refer to the joint or articulations in the human mid-foot consisting of the talus and navicular bones.

The terms "subtalar joint" or "STJ" is intended to refer to the joint or articulations in the human foot consisting of the talus bone and the calcaneus bone, as well as the interosseous talocalcaneal ligament.

The terms "calcaneocuboid" or "CC" are intended to refer to the joint or articulations in the human foot between the calcaneus and the cuboid bone.

The terms "metatarsophalangeal" or "MTP" are intended to refer to the joint or articulations of the human foot between the metatarsal and phalangeal bones.

The term "interphalangeal" is intended to refer to the joint or articulations of the human foot between phalangeal bones.

The term "arthrodesis" is intended to refer to a surgical immobilization of a joint by fusion of the adjacent bones.

The terms "arthrodesis" and "fusion" are used synonymously in the present application.

The term "osteotomy" is intended to refer to a surgical incision or transection of a bone.

The various embodiments of the present disclosure will be described in greater detail with reference to the accompanying drawings. It is not intended, nor should it be construed, that the scope of the embodiments be limited to the described features, materials, physical or dimensional specifications, arrangements, or uses. Rather, it is intended that the scope of the embodiments described be confined only to the claims appended hereto or as may be amended during prosecution of this application.

Figure 3:
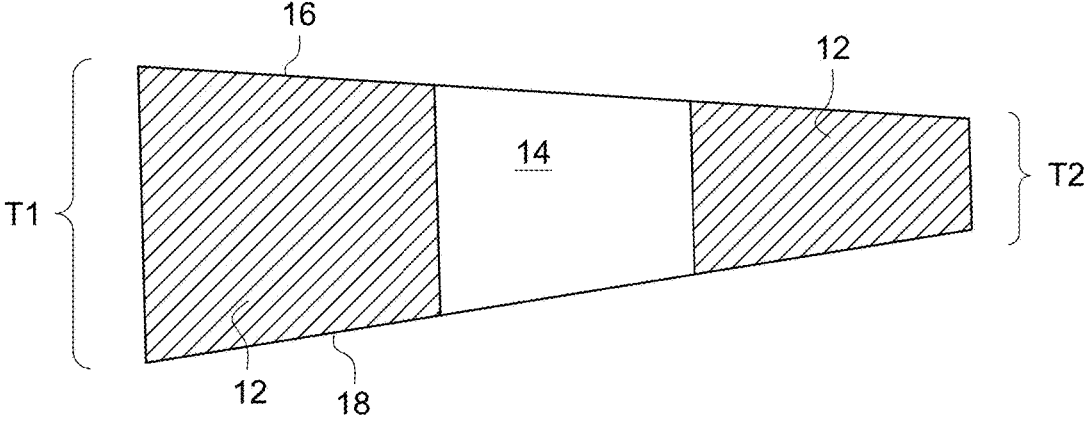
FIG. 3 is a cross-sectional view taken along line 3-3 of FIG. 1.

Turning now to FIGS. 1-4, there is illustrated an implant 10 for post-osteotomy spacing and realignment of bones in the mid-foot. The implant 10 generally consists of a wedge-shaped member 12 having a thickness taper 14 along at least one axis thereof such that a first thickness T1 at one end of the implant 10 is greater than a second thickness T2 at a second end of the implant 10, as illustrated in FIG. 3. The wedge-shaped member 12 has two opposing surfaces 16, 18, that are configured to abut opposing surfaces of bone 20, 22 post-osteotomy. The wedge-shaped member 12 may have any suitable geometric configuration, e.g., circular, elliptical, ovular, polygonal, annular, or the like along, at each of the two opposing surfaces 16, 18, thereof. The wedge-shaped member is made of a biocompatible material that permits and/or promotes bone ingrowth and/or acts as a degradable scaffold for bone growth. The biocompatible material may be metal, ceramic, composites, polymer, or a synthetic bone growth matrix, or combinations thereof. Suitable metals include shape memory alloys such as nickel-titanium based alloys, stainless steel, cobalt-based alloys, and titanium. The metal may be porous such as with sintered metals or may be surface treated to create osteophilic bone growth sites. Surface treatment may include altering the topography of metal or may include coatings that promote bone growth, or both. Ceramics may include, for example, alumina, zirconia, alumina composites, or oxidized zirconium composites. Synthetic bone growth matrices include, for example, hydroxyapatite, tricalcium phosphate, calcium sulfate, or combinations thereof. Polymers may be resorbable and may include, for example, polylactides, polyglycolides, polycaprolactone, cellulose, chitosan, collagen, hyaluronan, or fibrin.

In accordance with one embodiment, the wedge-shaped member 12, has a central opening 14 as shown in FIG. 1. The central opening 14 reduces the mass of the implant 10 and allows for fixation screws or wires to pass through the implant 10 to compress the osteotomy across the implant 10.

The taper of the wedge-shaped member 12 is preferably either fixed at a predefined angle or is adjustable post-implantation. The taper may be adjustable by providing an expandable shape memory material for the wedge-shaped member 12, such as NITINOL, a nickel-titanium alloy. It is well known in the art of shape memory materials that the shape memory properties of NITINOL are controllable by adjusting the stoichiometry of the atomic ratios of nickel-titanium and any other alloying metals that may be added during fabrication of the NITINOL material. Thus, both the shape and the kinetics of expansion may be controlled by selecting the appropriate stoichiometry of the shape memory material.

Figure 4:
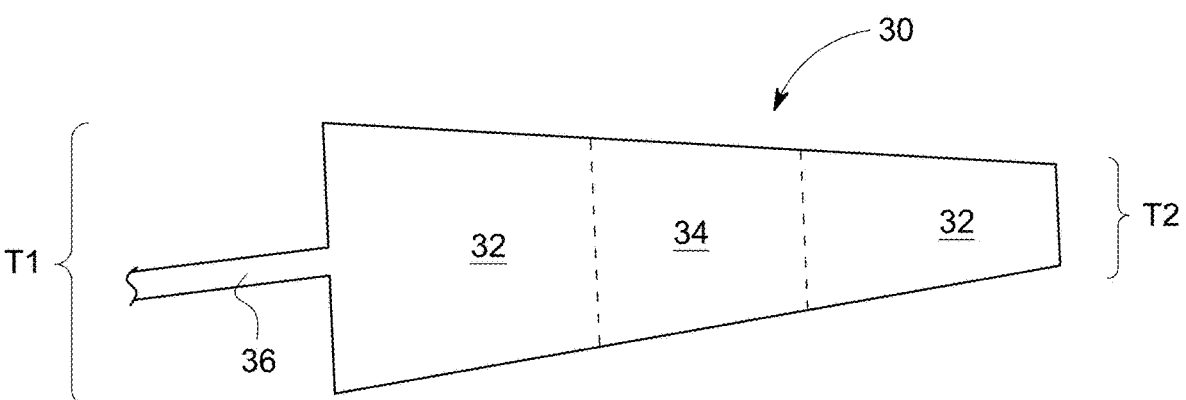
FIG. 4 is a side elevational view of a biocompatible wedge implant balloon in accordance with the present disclosure.

Alternatively, as illustrated in FIG. 4, the wedge-shaped member 30 may have an osmotic pump or other motive force generating device operably associated with the wedge-shaped member 30. For example, the osmotic pump may reside internally within the wedge-shaped member or may be coupled with the wedge-shaped member to pump an expansive fluid into a chamber 32 within the wedge-shaped member 30 in a controlled manner to allow for expansion of the wedge-shaped member 30 over time. Other motive force generating devices are also contemplated. For example, the wedge-shaped member 30 may be made of an expansive resorbable material having an inner inflation chamber 32 that is operable coupled to an inflation port 36. The inflation port 36 is configured to operably couple to an inflation catheter or be configured as an injection port to introduce an inflation fluid, molding material, and/or other material into the inner inflation chamber to adjust the taper of the wedge-shaped member 12. The molding material may be bone cement or a biologic. Bone cements and biologics are known in the orthopedic surgical field and include, for example, compounds such as polymethylmethacrylate based cements, calcium phosphate osteo-cements, calcium sulfates, or glass polyalkenoate (ionomer) cements. The bone cement may, optionally, have an antibiotic compounded therewith. Like wedge-shaped implant 10, wedge-shaped member 30 may have a taper along its longitudinal axis such that a first thickness T1 at one end of the implant 30 is greater than a second thickness T2 at a second end of the implant 30, as illustrated in FIG. 4.

Where a molding material is supplied to the inflation chamber of the wedge-shaped member 12, the wedge-shaped member 12 will conform to the space between adjacent bones and may either be left in-situ in its inflated state or may be removed to allow for in-suite manufacture of a conforming wedge-shaped member 12 that matches spacing and conformation of the patient's bones to be fused.

The wedge-shaped members 10, 30 may be wholly or partially made of a resorbable material to allow for total or partial bone ingrowth and incorporation of the wedge-shaped member 10, 30 at the fusion site. Similarly, bone cement may be osteophilic and/or porous to promote bone ingrowth.

Still again alternatively, the wedge-shaped member may have MEMS (Micro-Electromechanical Systems) devices operably associated therewith that are actuatable by external programming to adjust the degree of taper of the wedge-shaped member.

Figure 17A:
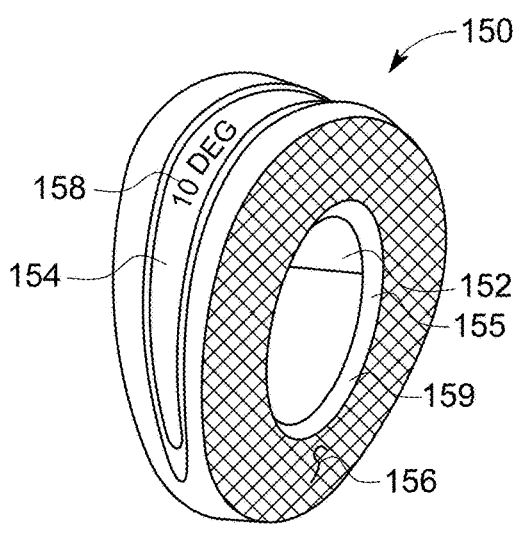
FIG. 17A is a perspective view of an alternative embodiment of a wedge implant system in accordance with the present invention
Figure 17B:
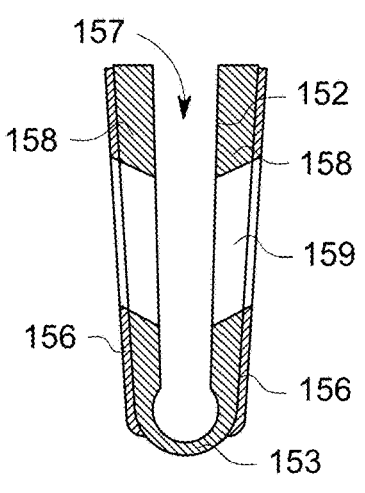
FIG. 17B is a side elevational cross-sectional view of a wedge implant sleeve component of the wedge implant system in accordance with the present invention.
Figure 17C:
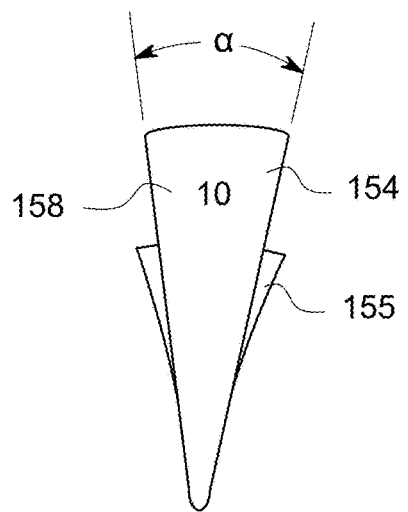
FIG. 17C is a side elevational view of a first shim component of the wedge implant system of the present invention.
Figure 17D:
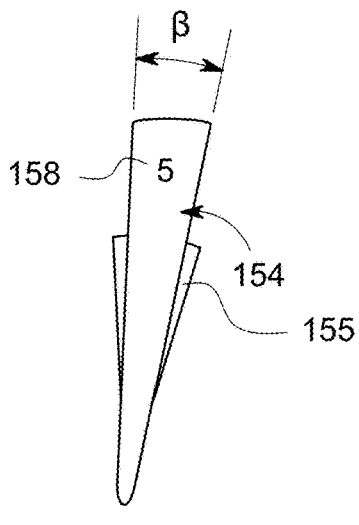
FIG. 17D is a side elevational view of a second shim component of the wedge implant system of the present invention.
Figure 17E:
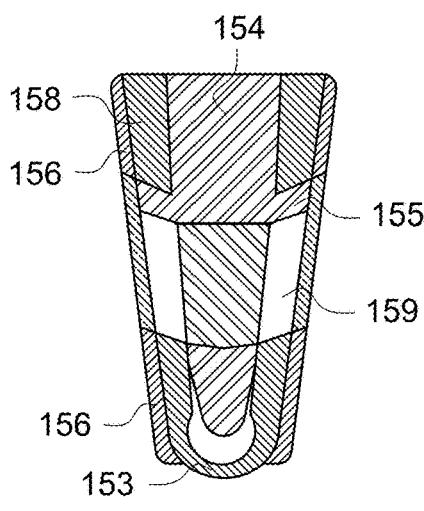
FIG. 17E is a side elevational cross-sectional view of an assembled wedge implant system in accordance with the present invention.

Conventional osteotomy wedges are available in a range of lengths, thicknesses, and angles to provide different degrees of correction angles. As illustrated in FIGS. 17A-17D, the present disclosure further provides an adjustable wedge implant system 150 that consists of a wedge implant sleeve 152 illustrated in FIGS. 17A and 17B, and a plurality of shims, illustrated in FIGS. 17A, 17C and 17D have a range of correction angles. The variability in correction angles is achieved by employing the implantable sleeve 152 and a plurality of the wedge shims 154 that are placed into an opening 157 in the sleeve 152. FIG. 17E illustrates wedge shim 154 engaged within shim opening 157 of sleeve 152 and seated therein.

The wedge implant system 150 has sleeve 152 having a shim opening 157 configured to accept one or more of the shims 154 therein that bear against lateral walls 158 of sleeve 152 and expand the sleeve 152 to an angle corresponding to the one or more shims 154. Each of the shims 154 may have a protrusion 155 that engages with a mating recess 159 in the sleeve 152 to secure the shim 154 within sleeve 152.

The sleeve 152 has external or bone-contacting osseointegration surfaces 156 on lateral walls 158 thereof and has a hinged region 153 that connects the lateral walls 158 to each other and permits the shim opening 157 to expand and contract as different angled shims 154 are placed in the shim opening 157 to adjust a correction angle of the osteotomy. Hinge region 153 may be achieved by configuring the hinge region 153 to have a thickness that is less than a thickness of the lateral walls 158 of the sleeve 152. Alternatively, the hinge region 153 of the sleeve 152 may be made with a material having a greater modulus of elasticity than the lateral walls 158 of the sleeve 152. Finally, the hinge region 153 of the sleeve 152 may be made of a shape memory material, such as nitinol, other shape memory or superelastic metal alloys, or shape memory or superelastic polymers. A non-limiting example of a construction of the sleeve is to form the body of the sleeve, including the lateral walls 158 and the hinge region 153, of a polymer, for example, polyether ether ketone (PEEK) or other biocompatible polymer or metal, then coat outer, bone contacting surfaces of the lateral walls with an osseo-integrative material, such as porous titanium or porous tantalum, including alloys thereof.

The plurality of shims 154 will have a range of angles. Based upon conventional osteotomy wedges, the plurality of shims may have an angle range between about 6- to about 14-degrees but may also have an angle range between about 4 to about 16 degrees, or about 2 to about 18 degrees or up to about 20-degrees. The plurality of shims 154 may be provided in 1-to-5-degree increments, preferably with 2-degree increments. For example, the plurality of shims 154 may come in 2-degree increments with the plurality of shims having 6-, 8-, 10-, 12-, and 14-degree angles. The shims may be employed individually or in multiples to achieve a desired angle of correction. Where multiple shims 154 are employed, the shims may be stacked within the shim opening 157 to allow for better correction resolution with a reduced number of shims 154. For example, if a 22-degree correction is required, a 14-degree shim 154 may be combined with an 8-degree shim 154, with both being stacked within the shim opening of the sleeve. Each of the shims 154 may, optionally, have an indica 158 corresponding to the angle α, β, of the corresponding shim 154.

Those skilled in the art will understand and appreciate that the plurality of shims 154 may be provided with a wide variety of angles α, β, and angle increments among the plurality of shims 154. For example, a total of 14-degree correction may be achieved with four stackable shims having 6-, 2-, 2-, and 4-degrees correction. Alternatively, a total of 16-degree correction may be achieved with five stackable shims 154 having 6-, 1-, 2-, 3-, and 4-degrees of correction. Furthermore, a total of 18-degree correction may be achieved with four stackable shims 154 having 6-, 2-, 4-, and 4-degrees correction. It will be understood that a wide variety of combinations of individual shim angles and numbers of shims may be provided to achieve a total stacked shim angular correction, and that the foregoing examples are not intended to limit the combinations of shim angles or total shim angle correction.

Figure 19:
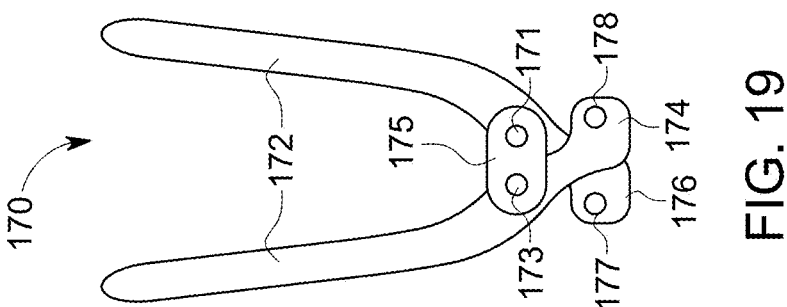
FIG. 19 is a side elevational view of a second embodiment of an arcuate orthopedic distractor in accordance with the present invention.
Figure 18B:
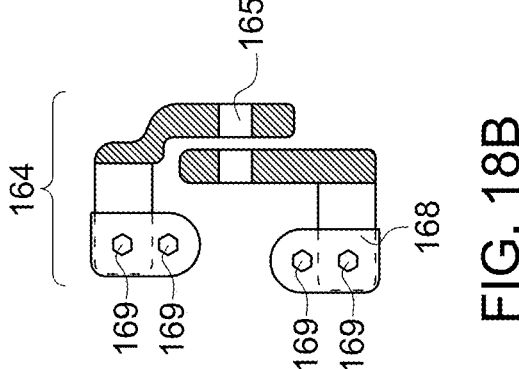
FIG. 18B is a top elevational partial cross-sectional view taken along line 18B-18B of FIG. 18A.
Figure 18A:
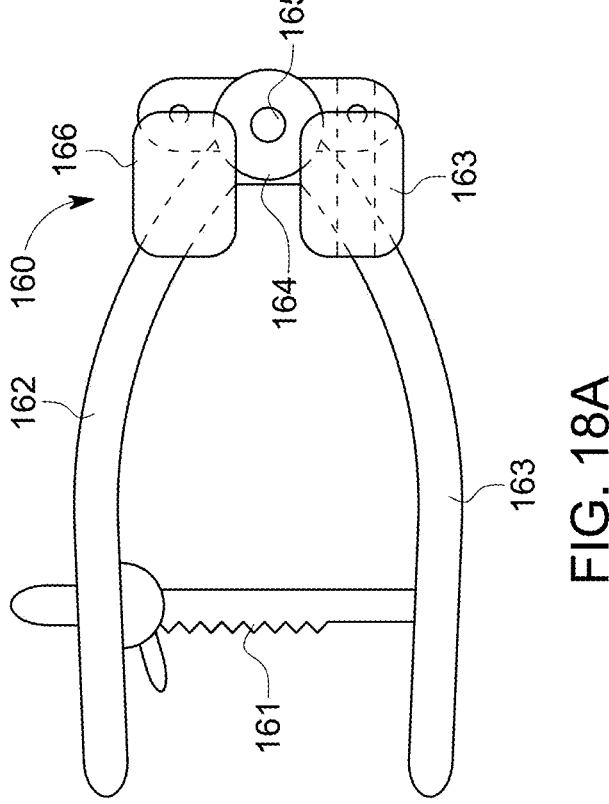
FIG. 18A is a perspective view of a first embodiment of an arcuate orthopedic distractor in accordance with the present invention.

According to a procedure for implanting the disclosed sleeve and shims, there is also disclosed an arcuate distractor instrument 160 as shown in FIGS. 18A and 18B. An alternative embodiment of an arcuate distractor instrument 170 is illustrated in FIG. 19. Both arcuate distractor instruments 160, 170, permit the surgeon to make an osteotomy partially through the bone leaving the bone intact on the opposing surface of the bone to act as a bone hinge for distraction of the osteotomy. For example, where the bone is accessed dorsally, the bone hinge is formed at the plantar surface of the bone. Current procedures involve impacting trial wedges into the osteotomy to assess the needed correction and then implanting the appropriate final implant. This repeated impaction of the osteotomy increases the risk of fracture to the bone hinge at the plantar surface of the bone. An additional risk of repeated impaction of the trial wedges is the tendency of the trial wedges to smooth the lateral bone surfaces resulting in compromised retention of the final implant within the osteotomy.

Existing osteotomy distractors typically operate by opening in a parallel fashion such that the osteotomy is also opened in a parallel manner. In use, osteotomy distractors are joined to Kirschner wires, or K-wires, which are pins inserted into drilled openings in surfaces of the bone prior to making the osteotomy cut. Once the K-wires are placed, and the osteotomy cut made, conventional distractors are then engaged with the K-wires and the distractor moves the K-wires in a parallel manner as the distractor opens, which forces the osteotomy to also open or distract in a parallel manner. This parallel movement of the osteotomy is not appropriate for implanting the adjustable wedge implant of the present disclosure which requires an arcuate opening of the osteotomy.

FIGS. 18A-19 illustrate an arcuate distractor 160, 170 and system for creating a wedge osteotomy on a dorsal surface of bone in accordance with the present disclosure. The arcuate distractor system of the present disclosure consists generally of an arcuate and angular distractor having a pair of articulating handles, at least one pivot joining the pair of articulating handles, opposing jaws, each jaw extending from one of the articulating handles, and a distractor head. An optional osteotomy cutting guide may also be provided. Osteotomy cutting guide may be a separate element from the arcuate distractor, may be incorporated into the distractor head, or may be configured to removably couple to the distractor head. The osteotomy cutting guide controls both placement and depth of the osteotomy cut, and the distractor opens the osteotomy to allow placement of the wedge implant without the need for using trial wedges.

Arcuate distractor 160 consists generally of a pair of handles 162, 163 that are joined by a pivot 165. A distractor head 164 projects from a distal end of each of the handles 162, 163. The distractor head 164 may project perpendicular to or parallel to a longitudinal axis of each of the handles 162, 163 with which it is associated. The distractor head 164 has two flanges 166, 168, with each flange 166, 168 extending from a corresponding handle 162, 163. Flanges 166, 168 articulate in an arcuate manner about the pivot 165 that couples each of the handles 162, 163 and corresponding flanges 166, 168. Each flange 166, 168 has at least one opening 169 that passes through the flange 166, 168. Each opening 169 has an opening diameter configured to receive a K-wire there through. Optionally, the handles 162, 163 may be interconnected by mechanism 161 that extends between the handles 162, 163 and ratchets and/or locks the handles 162, 163, and therefore the distractor head 164, into a fixed position. Optionally, mechanism 161 may have indicia marked thereupon to provide the surgeon with a visual indicator of the opening angle of the distractor head 164.

FIG. 19 illustrates a second embodiment of an arcuate distractor 170. Arcuate distractor 170 has a pair of handles 172, with each handle 172 having a flange 174, 176 projecting from a distal end thereof. A pivot plate 175 interconnects each of the handles 172 proximal to the flanges 174, 176 and connects to each handle 172 with a pivot 171, 173 at opposing end of the pivot plate 175. In this manner, pivot 171 couples pivot plate 175 to a first handle 172 and pivot 173 couples pivot plate 175 to a second handle 172, such that there are two pivot points for handles 172 that allow for arcuate movement of the flanges 174, 176 when the handles 172 are actuated. Each of the flanges 174, 176 has at least one opening passing there through, with each of the at least one has a diameter configured to accept a K-wire there through.

Figures 20A, 20B, 21:
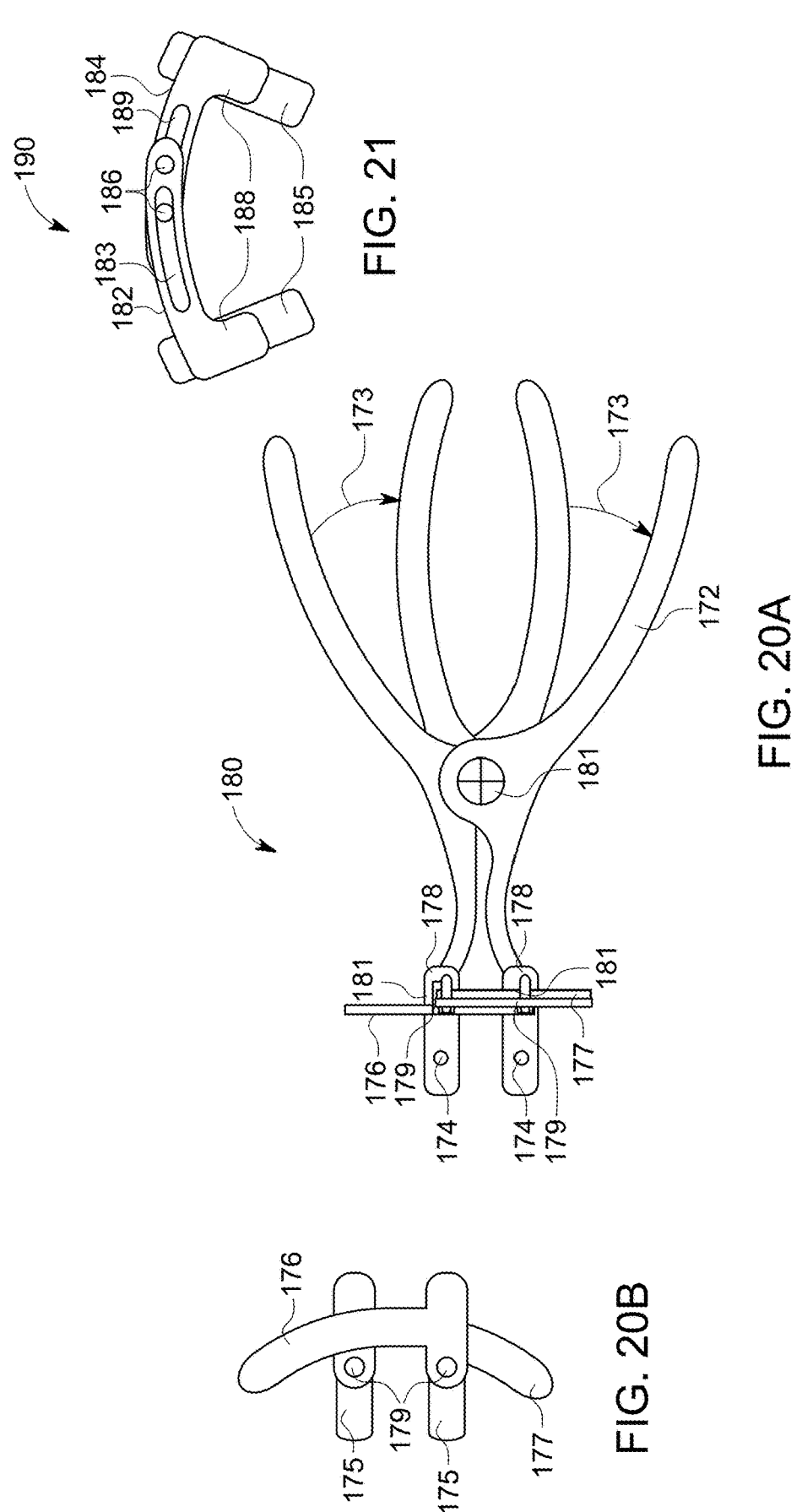
FIG. 20A is a side elevational view of a third embodiment of an arcuate orthopedic distractor in accordance with the present invention.
FIG. 20B is a top elevational fragmentary view of a first arcuate guide of the third embodiment of the arcuate ortho- pedic distractor of FIG. 20A.
FIG. 21 is a top elevational fragmentary view of a second arcuate guide of the third embodiment of the arcuate ortho- pedic distractor of FIG. 20A.
Figures 22A, 22B, 22C, 22D, 22E, 22F:
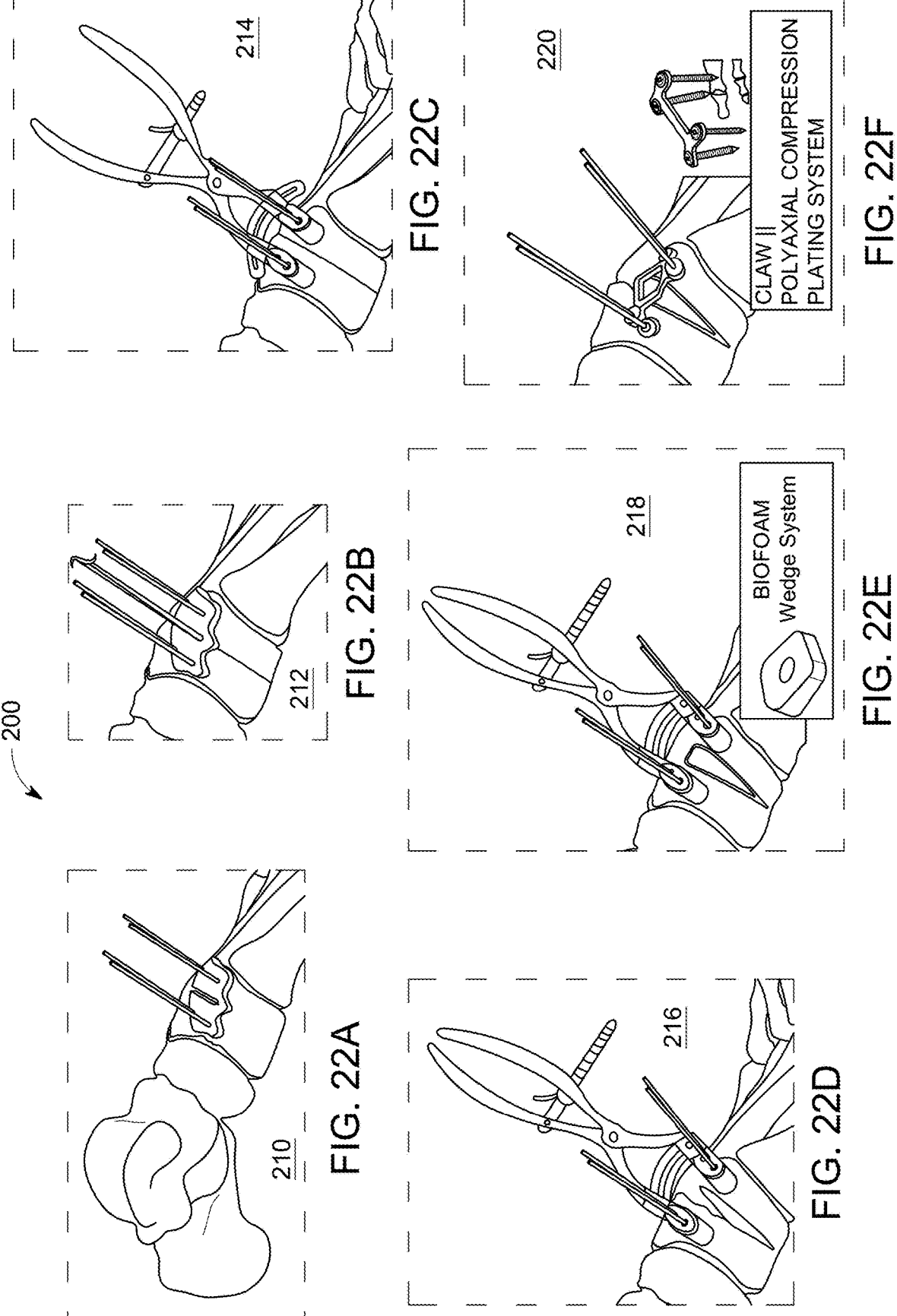
FIGS. 22A to 22F are perspective views illustrating sequential method steps of a wedge implant arthrodesis.

FIGS. 20A, 20B and 21 illustrate further embodiments of an arcuate distractor head 180, 190. Unlike, arcuate distractors 160, 170, each of distractor heads 180, 190 have two reciprocating and cooperating arcuate members 176, 177; a first arcuate member is coupled to a first jaw member 178 and a second arcuate member is coupled to a second jaw member 178. Each of the arcuate members 176, 177 may be substantially planar such that they are slidably engaged with each other and be configured to reciprocate relative to each other along a substantially common plane. Of course, other configurations of the two arcuate members 176, 177 are intended and contemplated by the present disclosure, including, for example cooperating and interfacing wires, tubes, or the like. Each of the jaw members 178 are project from a handle 172 of the distractor. In FIGS. 20A and 20B a distractor head 180 consists of a first arcuate member 176, and a second arcuate member 177. Each of the first arcuate member 176 and the second arcuate member 177 have a pivot 179 that permits the respective first and second arcuate members 176, 177 to rotate about the respective pivot 179. Each pivot 179 rotatably joins one of the first and second arcuate members 176, 177 to a connector member 175 that couples each of the first arcuate member 176 and the second arcuate member 177 to a jaw member 178 of the distractor. Jaw members 178 open and close by rotating around handle pivot 171 as the handles 172 are translated between and open and closed position, as indicated by arrows 173.

As shown in FIG. 21, distractor head 190 consists of two arcuate members 182, 184. Each of the two arcuate members 182, 184 may be substantially planar such that they are slidably engaged with each other and be configured to reciprocate relative to each other along a substantially common plane. Of course, other configurations of the two arcuate members 182, 184 are intended and contemplated by the present disclosure, including, for example cooperating and interfacing wires, tubes, or the like. Each of the two arcuate members 182, 184 have a guide member 186 joined thereto that engages with an arcuate slot 183, 187 in each of the two arcuate members 182, 184, respectively. Guide member 186 may be a pin, a flange, a detent, or other similar projection from a respective arcuate member 182, 184.

Each of the first and second arcuate members 176, 177, have a guide collar 181 that projects perpendicular to a plane of the respective arcuate member 176, 177. Guide collar 181 is configured to allow a respective first or second arcuate member 176, 177 to pass through the guide collar 181 and longitudinally translate through the guide collar 181. Thus, the guide collar 181 on the first arcuate member 176 is configured to accommodate the second arcuate member 177 to pass there through, and the guide collar 181 on the second arcuate member 177 is configured to accommodate the first arcuate member 176 to pass there through.

Distractor heads 180, 190 may be coupled to the jaw members 178 in a co-planar or perpendicular manner, or have other orientations relative to the longitudinal axis of the jaw members 178. A perpendicular orientation of distractor heads 180, 190 allows the surgeon to manipulate the distractor in the sagittal plane of the foot, whereas a co-planar orientation of the distractor heads 180, 190 allows the surgeon to manipulate the distractor in the horizontal plane of the foot.

The angular and arcuate movement of an arcuate distractor 160, 170, 180, 190 opens the wedge osteotomy while limiting stress applied to the bone hinge during opening of the osteotomy. Guide indicators may be provided on the distractor to indicate angular opening markings and/or on the cutting guide to indicate length and depth of the osteotomy cut.

A wedge osteotomy method 200 is illustrated in FIGS. 22A to 22F. According to method 200, K-wires are placed at the osteotomy site and a cutting guide is placed over the K-wires at step 210. An osteotomy is performed using the cutting guide at step 220. The osteotomy may be through a dorsal surface of the bone leaving an uncut region of the bone adjacent the plantar surface of the bone that serves as a fulcrum for the wedge osteotomy. Next, after removal of the cutting guide, an arcuate distractor is placed over the K-wires and approximated to the bone on either side of the wedge osteotomy at step 214. Actuation of the distractor at step 216 opens the wedge osteotomy, and the osteotomy wedge or the osteotomy wedge system of the present disclosure is placed in the wedge osteotomy at step 218. A compression plate may be employed across the wedge osteotomy to compress and secure the osteotomy wedge system in the wedge osteotomy.

Figure 5A:
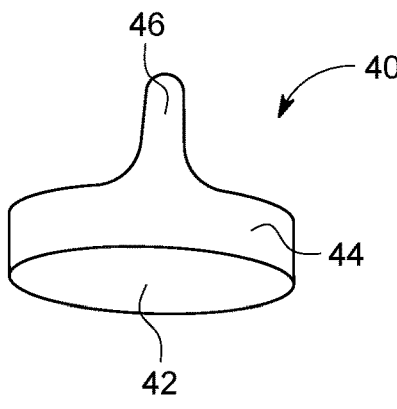
FIG. 5A is an end elevational view of a slot insert implant for transverse arthritis arthroplasty in accordance with present disclosure.
Figure 5B:
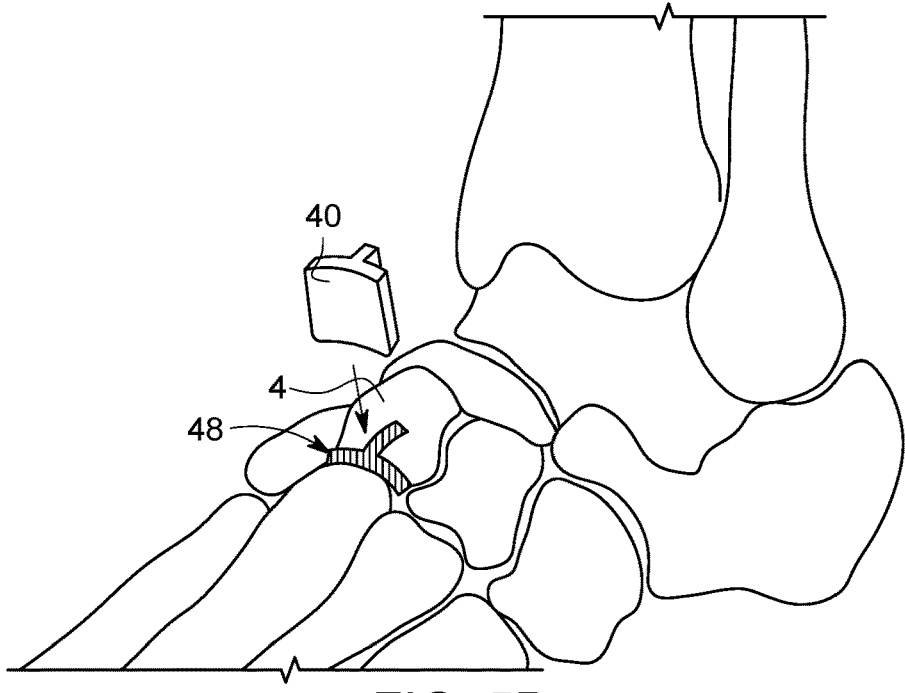
FIG. 5B is a partially exploded perspective view of the slot insert implant of FIG. 5A and its positional relationship with the mid-foot architecture.

Turning to FIGS. 5A and 5B, 23A-23D, 24, and 27A-34 there is illustrated a transverse arthritis arthroplasty system that is particularly well-suited for fusion of the $2^{nd}$ through 5th mid-foot joints, including the TMT, MTP, NC, TN, STJ, and CC joints. It will be understood by those skilled in the art that the arthritis arthroplasty system has equal applicability in similar joints of the hand and wrist. The arthritis arthroplasty system consists generally of inserts 40 configured to be placed in the articular space between adjacent bones after the opposing bones and the articular surfaces of the bones have been resected as illustrated in FIG. 5B. Insert 40 is configured to resurface each of the articular surfaces of the resected bones at the $2^{nd}$, $3^{rd}$, $4^{th}$, or $5^{th}$ mid-foot joints. Insert 40 may be made of a metal material with a ceramic or polymeric articular surface or may be a ceramic or polymeric material with a metal articular surface. Deformity correction may be further enhanced with variable wedges in conjunction with insert 40. It is intended and will be understood that reference to mid-foot joints is exemplary only and that the scope of the arthritis arthroplasty system is intended to include other foot, ankle, hand, and/or wrist joints.

Insert 40 consists generally of an articular section 42, an osteo-interface section 44, and a projection 46 projecting outwardly from the osteo-interface section 44. As exemplified in FIG. 5B, the insert 40 is placed into a recess 48 surgically formed in a bone, in this case a cuneiform bone 2, with the articular section 42 interfacing with the metatarsal bone 4, the osteo-interface section 44 interfacing with the recess 48, and the projection 46 interfacing with a mating portion of recess 48 in the cuneiform bone 2. Recess 48 is configured to have a geometry that mates with the insert 40, including the osteo-interface section 44 and the projection 46. While FIG. 5B illustrates a dorsal approach for implantation of insert 40, it will be understood that a plantar approach may alternatively be employed.

Figures 23A, 23B, 23C, 23D:
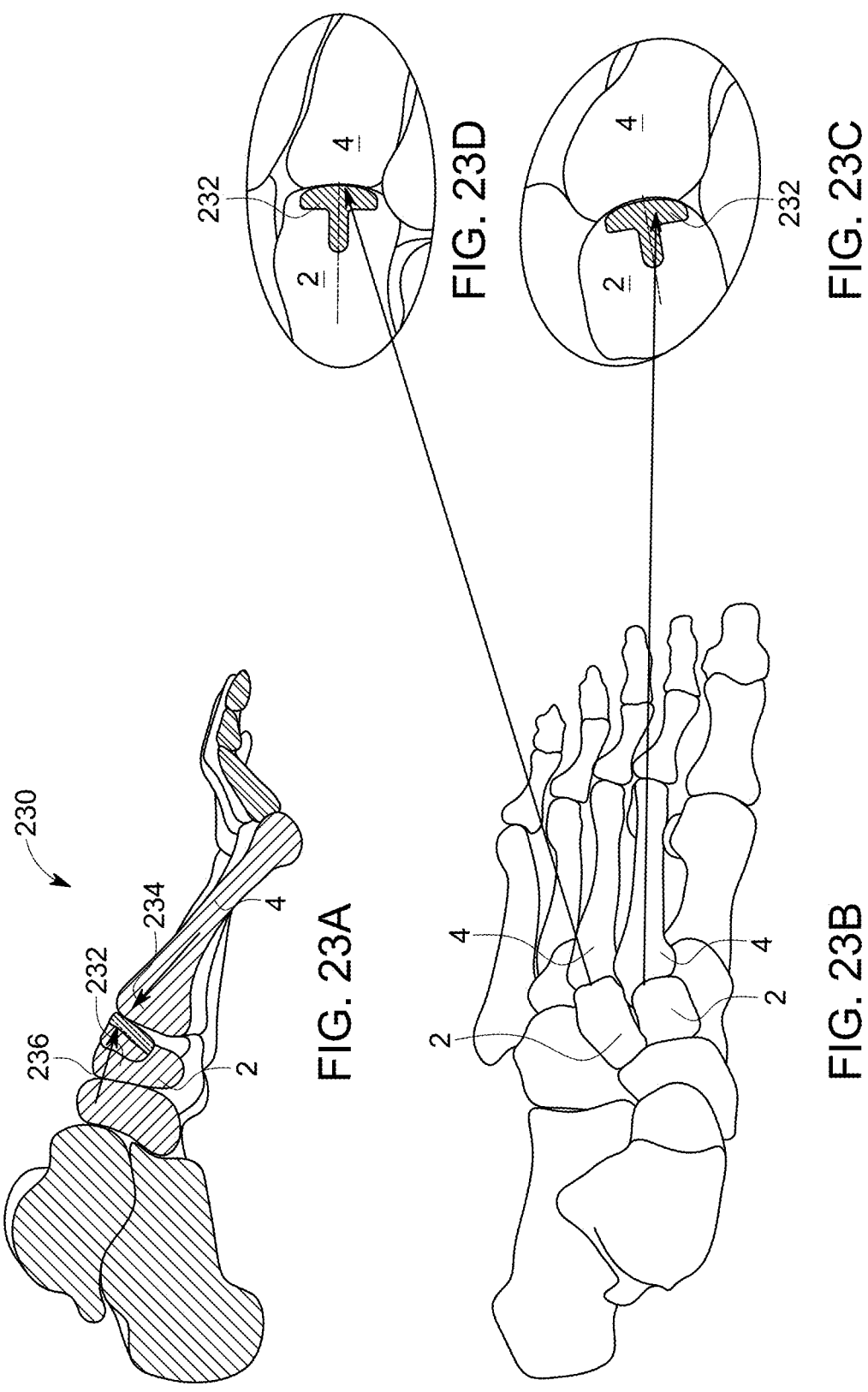
FIG. 23A is a lateral view of a mid-foot architecture illustrating a slot insert implanted in the tarsometatarsal joint and longitudinal forces applied to the slot insert.
FIG. 23B is a dorsal view of the tarsometatarsal joint of the mid-foot architecture.
FIG. 23C is a dorsal view of a slot insert implanted in the $2^{nd}$ tarsometatarsal joint.
FIG. 23D is a dorsal view of a slot insert implanted in the $3^{rd}$ tarsometatarsal joint.

FIGS. 23A to 23D are alternative illustrations showing implantation of an insert 232, in the $2^{nd}$ TMT joint (FIG. 23C) and/or the $3^{rd}$ TMT joint (FIG. 23D), showing the cuneiform bones 2 and the metatarsal bones 4 with the insert 232 implanted into a cuneiform bone 2 in each instance. FIG. 23A illustrates the respective force vectors 234, 236 acting on the insert 232 once it is implanted.

FIG. 24 is an illustration of an alternative embodiment of insert 232 implanted in both a cuneiform bone 2 and a metatarsal bone 4 and showing the articular surface 234 and the projection 236 of the implanted insert 232 engaged within the recesses 48 formed in each of the cuneiform bone 2 and metatarsal bone 4. Those skilled in the art will appreciate that insert 232 may be implanted into one bone of a joint, i.e., a hemi-arthroplasty, or both bones of a joint.

FIGS. 25 and 26 illustrate a burr guide 240 useful in forming recess 48 to accommodate implantation of inserts 40, 232. Burr guide 240 consists of a guide plate 242 that has guide recess 244 bounded by the guide plate 242 and a burr opening 246 in a lower surface of the guide plate 242. The guide plate 242 has a plurality of fixation openings 243 passing there through that are configured to receive a K-wire or other fixation to fix the position of the guide plate 242 relative to the bone 2 being cut. A burr 245, which may optionally have a depth guide 248 and spring 247, is mounted on a burr plate 249. Guide recess 244 receives the burr plate 249 and allows the burr plate 249, as well as the burr 245, to be moved by the surgeon within the guide recess 244. The burr 245, which is engaged with a rotary drill (not shown), passes through the burr plate 249 and the burr opening 246 to contact and cut the bone 2. By moving the burr 245 on the burr plate 249 within the guide recess 244, the burr 245 will track the configuration of the burr opening 246 and cut the bone to a cut geometry and depth that corresponds to the configuration of the burr opening 246 and/or the configuration of the guide recess 244.

It will, of course, be understood that the configuration of the burr guide 240 will correspond to the geometry of the cut desired in the bone 2. Thus, for any given configuration of insert 40 in FIGS. 5A and 5B, insert 232 in FIG. 24, or any of inserts 250, 260, 270, 280, 290, 300, 310, shown in FIGS. 17A to 33, a corresponding configuration of the burr guide 240 will be employed.

For purposes of brevity, hereinafter all embodiments of the disclosed inserts will refer to "insert, e.g., XX"; all embodiments of the disclosed articular surfaces will refer to "articular surface, e.g., XX"; all embodiments of the disclosed osseo-interfacing surfaces will refer to "osseo-interfacing surface, e.g., XX"; and all embodiments of the disclosed projections will refer to "projection, e.g., XX," where XX is a reference numeral corresponding to one embodiment of the respective element as illustrated in one or more of FIGS. 5A and 5B, FIG. 24, an FIGS. 17A to 33.

Common to all embodiments of the insert, e.g., 40, is the articular surface, e.g. 42, the osteo-interfacing surface, e.g., 44, and the projection, e.g., 46 from the osteo-interfacing surface 44. The overall configuration of the insert is that it has a generally T-shaped profile when viewed from a plantar or dorsal view. In each of the disclosed embodiments of insert 40 in FIGS. 5A and 5B, insert 232 in FIG. 24, or any of the embodiments of inserts 250, 260, 270, 280, 290, 300, 310, shown in FIGS. 17A to 33 the articular surface, e.g., 262 (FIGS. 28A and 28B) is either planar or has a radius. The osteo-interfacing surface 264 (FIGS. 28A and 28B) and the projection 266 (FIGS. 28A and 28B) are configured to interface with the cut in bone 2, 4 and join thereto. The articular surface may be made of metal, polymer, composite, ceramic, or other material suitable for use as an articular interface. The osteo-interfacing surface and the projection may be made of metal, polymer, composite, ceramic, or other material that preferably has osseointegration capabilities. Suitable osteointegrative materials include, for example, porous titanium or porous tantalum, including alloys thereof.

Figures 27A, 27B, 28A, 28B, 29A, 29B, 30A, 30B, 31A, 31B, 32, 33, 34:
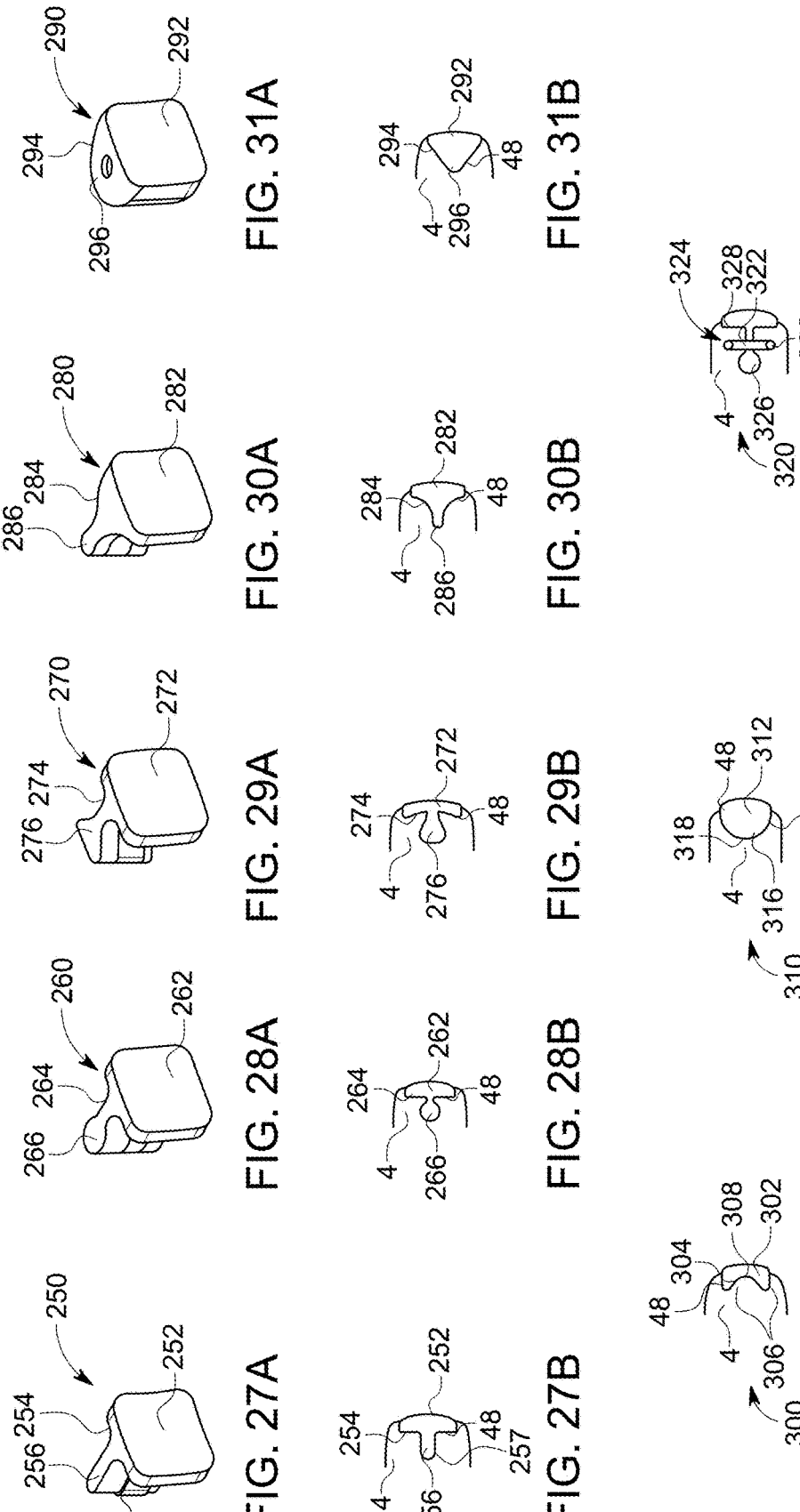
FIG. 27A is a perspective view of a first embodiment of a slot insert in accordance with the present invention.
FIG. 27B is a dorsal view of the second embodiment of the slot insert implanted in a cuneiform bone at a tarsometa- tarsal joint in accordance with the present invention.
FIG. 28A is a perspective view of the second embodiment of a slot insert in accordance with the present invention.
FIG. 28B is a dorsal view of the third embodiment of the slot insert implanted in a cuneiform bone at a tarsometatarsal joint in accordance with the present invention.
FIG. 29A is a perspective view of a fourth embodiment of a slot insert in accordance with the present invention.
FIG. 29B is a dorsal view of the fourth embodiment of the slot insert implanted in a 9cuneiform bone at a tarsometa- tarsal joint in accordance with the present invention.
FIG. 30A is a perspective view of a fifth embodiment of a slot insert in accordance with the present invention.
FIG. 30B is a dorsal view of the firth embodiment of the slot insert implanted in a cuneiform bone at a tarsometatarsal joint in accordance with the present invention.
FIG. 31A is a perspective view of a sixth embodiment of a slot insert in accordance with the present invention.
FIG. 31B is a dorsal view of the sixth embodiment of the slot insert implanted in a cuneiform bone at a tarsometatarsal joint in accordance with the present invention.
FIG. 32 is a dorsal view of a seventh embodiment of the slot insert implanted in a cuneiform bone at a tarsometatarsal joint in accordance with the present invention.
FIG. 33 is a dorsal view of an eighth embodiment of the slot insert implanted in a cuneiform bone at a tarsometatarsal joint in accordance with the present invention.
FIG. 34 is a dorsal view of a ninth embodiment of a slot insert in accordance with the present invention.
Figures 35, 36, 37, 38, 39, 40:
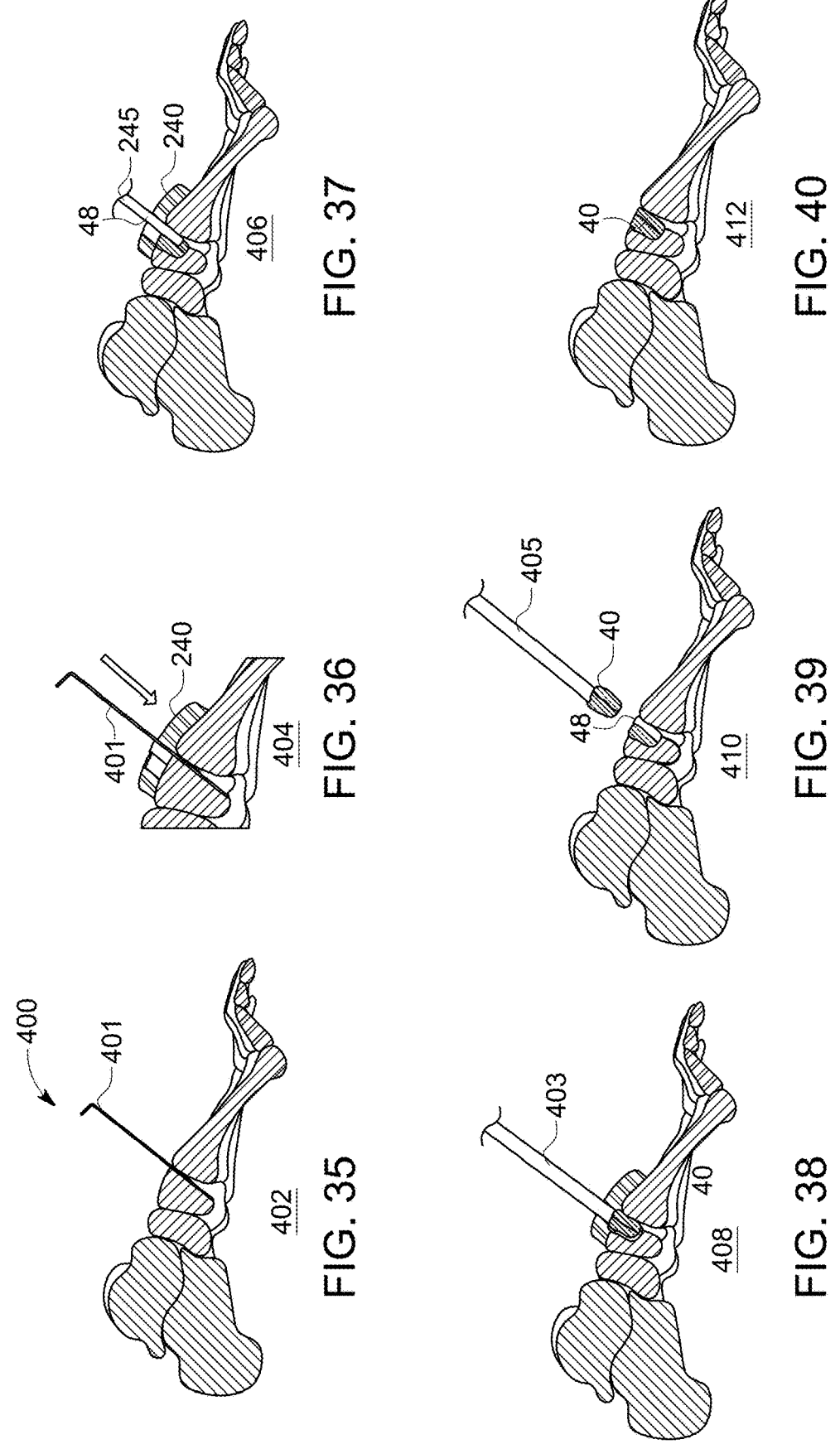
FIGS. 35 to 40 are lateral views illustrating sequential method steps for implanting a slot insert into the tarsometa- tarsal joint in accordance with the present invention.

Insert 250 in FIGS. 27A and B consists of a substantially T-shaped body having an articular surface 252, an osseo-facing surface 254 that abuts the bone when implanted, and projection 256 that seats the insert 250 in a mating recess 48 formed in the bone 4. At least one rib 257 extends around the projection 256 to engage with the bone in the mating recess 48 and assist in securing the insert 250 within the recess 48.

Insert 260 in FIGS. 28A and 28B also consists of a generally T-shaped body having an articular surface 262, an osseo-facing surface 264 that abuts the bone 4 when implanted, and projection 266 that seats the insert 260 in a mating recess 48 formed in the bone 4. The projection 260 has a rounded or filleted end profile that mates with a comparable rounded portion of the projection recess 48 in bone 4. The engagement between the projection 266 and the projection recess 48 is conceptually similar to a lock-and-key configuration.

Insert 260 in FIGS. 28A and 28B also consists of a generally T-shaped body having an articular surface 262, an osseo-facing surface 264 that abuts the bone 4 when implanted, and projection 266 that seats the insert 260 in a mating recess 48 formed in the bone 4. The projection 260 has a rounded or filleted end profile that mates with a comparable rounded portion of the projection recess 48 in bone 4. The engagement between the projection 266 and the projection recess 48 is conceptually similar to a lock-and-key configuration.

Insert 270 in FIGS. 29A and 29B also consists of a generally T-shaped body having an articular surface 272, an osseo-facing surface 272 that abuts the bone 4 when implanted, and projection 276 that seats the insert 270 in a mating recess 48 formed in the bone 4. The projection 270 has a substantially polygonal transverse profile that mates with a comparable polygonal portion of the projection part of recess 48 in bone 4. The engagement between the projection 276 and the projection recess 48 is conceptually similar to a lock-and-key configuration.

Insert 280 in FIGS. 30A and 30B also consists of a generally T-shaped body having an articular surface 282, an osseo-facing surface 284 that abuts the bone 4 when implanted, and projection 286 that seats the insert 280 in a mating recess 48 formed in the bone 4. The projection 286 has a tapers along a chamfered surface 288 of the osseo-facing surface 284 rounded or filleted end profile that mates with a comparable rounded portion of the projection recess 48 in bone 4. The engagement between the projection 286 and the projection recess 48 is conceptually similar to a lock-and-key configuration.

Insert 290 in FIGS. 31A and 31B also consists of a substantially polygonal body having an articular surface 292, an osseo-facing surface 294 that abuts the bone 4 when implanted, and projection 296 that seats the insert 290 in a mating recess 48 formed in the bone 4. The projection 296 consists of a taper of the osseo-facing surface 294 that terminates in a vertex 298 of the insert 290. The recess 48 has a mating configuration that seats the osseo-facing surface 294 and the vertex 298 of insert 290. The engagement between the projection 296 and the projection recess 48 is conceptually similar to a lock-and-key configuration.

Insert 300 is shown in FIG. 32 and also consists of a body having an articular surface 302, an osseo-facing surface 304 that abuts the bone 4 when implanted, and at least two projections 306 that seat the insert 300 in a mating recess 48 formed in the bone 4. The osseo-facing surface 304 consists of a concave fillet 308 and the projections 306 extend into the bone 4 and bound lateral sides of the concave fillet 308. Each of the projections 306 may have any of a variety of transverse configurations, including pointed vertices, rounded surfaces, polygonal, or other similar configurations that increase surface area contact between the recess 48 of bone 4 and the osseo-facing surface 304 and projections 306 while facilitation a secure interface between insert 300 and bone 4.

Insert 310 is shown in FIG. 33 and also consists of a body having an articular surface 312, an osseo-facing surface 314 that abuts the bone 4 when implanted, and a projection 316 that seats the insert 310 in a mating recess 48 formed in the bone 4. The osseo-facing surface 314 consists of a convex rounded fillet 318 with projection 316 being formed by a region of the convex founded fillet 318 furthest from the articular surface 312.

Finally, insert 320 consists of a body having any configuration that includes an articular surface 322, an osseo-facing surface 324, a projection 326, and an affixation member 328. Affixation member 328 may be a staple, plate, screws, or the like that is placed over or into the projection 326 to assist in maintaining engagement between insert 320, recess 48, and bone 4.

In order to perform arthritis arthroplasty with the insert, e.g., 40, different joints of the mid-foot require different surgical approaches. For example, the TMT and MTP joints will require implantation of the inserts, e.g., 40, from a dorsal approach, whereas the NC and TN joints are best approached from a dorsal medial approach. The STJ implanted with insert, e.g., 40, through a medial/lateral/posterior approach, whereas the CC joint is implanted with insert 102 by a dorsal/lateral surgical approach.

The method 400 of implanting insert, e.g., 40, is illustrated in FIGS. 35 to 40. First, the joint, such as a TMT joint is surgically accessed, and a joint finder 401 is placed into the joint 402. Using joint finder 401 as a guide, a K-wire is placed through the joint finder 401 and a burr guide 240 is placed 404 over K-wire and approximated against the joint. K-wires may also be deployed in one or more of the opposing bones at the joint to further guide and positionally secure the burr guide 240 against the joint. Once the burr guide 240 is placed at the joint, a burr 245 is engaged with the burr guide 240 and recess 48 is formed 406. The depth and shape of recess 48 is then tested by using a trial insert, e.g. 40, mounted on instrument 403, and the fit and correction of trial insert, e.g., 40 is checked 408. Further reaming, drilling, or burring of recess 48, and checking 408 is repeated if required. Once the depth and shape of recess 48 and the fit of trial insert, e.g., 40 is verified, then the implant insert, e.g., 40 is inserted and fit 410 into recess 48 using insert instrument 405. Once the insert, e.g., 40, is fully implanted into the joint, insert instrument 405 is removed from the insert, e.g., 40, 412, and the surgical access site is closed.

The angle between the cuneiforms and metatarsals is variable. This angle often changes as the result of the injury or arthritic condition. The most common deformity is associated with a collapse of the midfoot which represents a dorsiflexion malposition. 1st TMT arthritis and deformity is a common problem and is treated with 1st TMT arthrodesis. The other midfoot joints are the 2nd, 3rd, 4th and 5th tarsometatarsal joints (TMT). Structurally and philosophically these are grouped into 2+3 TMT and 4+5 TMT. The 2nd and 3rd TMT joints are often arthritic in conjunction with 1st TMT arthritis.

Figure 41:
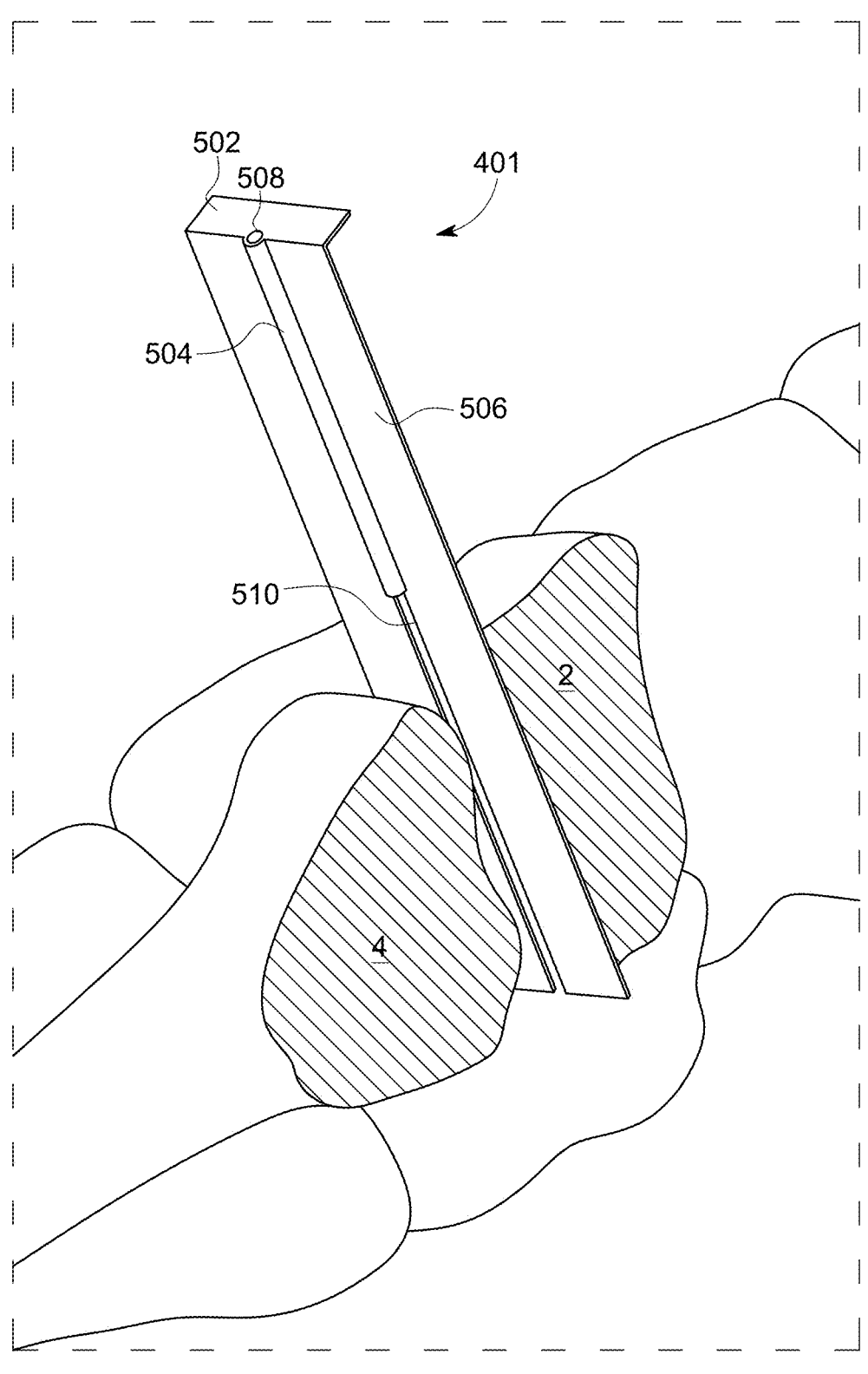
FIG. 41 is a perspective view of a joint finder instrument engaged with a TMT joint in accordance with the present disclosure.

As shown in FIG. 41, the joint finder 401 consists generally of an elongated planar member 506 having a handle portion 502 and a tubular guide 504 extending at least along at least a partial length of the elongated planar member

506. The handle portion 502 is positioned at a proximal end of the elongated planar member 506 and may have a substantially perpendicular orientation relative to the elongated planar member 506. A recess 508 is centrally located along a substantial mid-line of the elongated planar member 506 and extends at least partially along a longitudinal length of the elongated planar member 506. The tubular guide 504 may, optionally, be nested in the recess 508. Tubular guide 504 has its proximal opening accessible from the handle portion 502, and a distal opening is positioned such that a K-wire may be placed within the tubular guide 504 and be passed into the joint to act as a guide for a drill. Optionally, the elongated planar member 506 may have a slot 510 that extends from a distal end of the tubular guide 504 to a distal end of the elongated planar member 506. Tubular guide 504 is configured to accept a K-wire there through and guide the K-wire into the joint between bones 2, 4, for example the cuneiform bone 2 and the metatarsal bone 4. The elongated planar member 406 may, optionally, have graduation markings (not shown) to assist the surgeon with determining the depth of placement within the joint. It will be understood, however, that reference to the cuneiform bone 2 and the metatarsal bone 4 of the TMT joint is merely exemplary, and that the joint finder 401 may be employed in many different joints of the anatomic extremities, including the foot, ankle, legs, hands, and arms.

In use, the joint finder 401 will rest between the joint bones 2, 4 and is configured to articulate within the joint using the handle to both manipulate the joint finder 401 and aid in determining angular measurements between the bone and the joint axis. This permits the surgeon to define a pre-correction angle and features and plan for the appropriate angular correction. Once the angular correction is determined, the surgeon is then able to calculate the intended correction for both forming the recess 48 and the appropriate dowel, e.g., 40. From this point, the surgeon is then able to continue with the remainder of the steps of the joint arthrodesis.

Insert, e.g. 40, is configured to be joined to either or both of the opposing articular surfaces of the longitudinally adjacent bones, i.e., a hemi-arthroplasty in which the insert is in one bone vs. an arthroplasty in which the insert is in both bones. Insert, e.g., 40, may be adhesively joined to the resected bones, it may be inserted with a friction fit interface between bone and implant, an/or it may have an anchoring projection that is inserted into and affixed to a bore or recess formed in the articular surface of the resected bone, and/or the bone contacting surfaces may be configured, such as by texturing or porosity, to promote on-growth and/or ingrowth to the mating surface of insert, e.g., 40. Optionally, the insert, e.g., 40, is fixated to the bone via a retaining pin or projection that maintains the insert 102 in position relative to the bone so that movement of the insert, e.g., 40, is restricted. Such retaining pins may have a bead that frictionally seats the insert, e.g., 40, to the bone. Insert, e.g., 40, may be made of a ceramic or polymeric articular surface on a metal support or of a metal articular surface on a ceramic or polymeric support. Other materials and constructs for insert, e.g., 40, are also intended and contemplated as being included within the intended scope of insert, e.g., 40.

Figure 6:
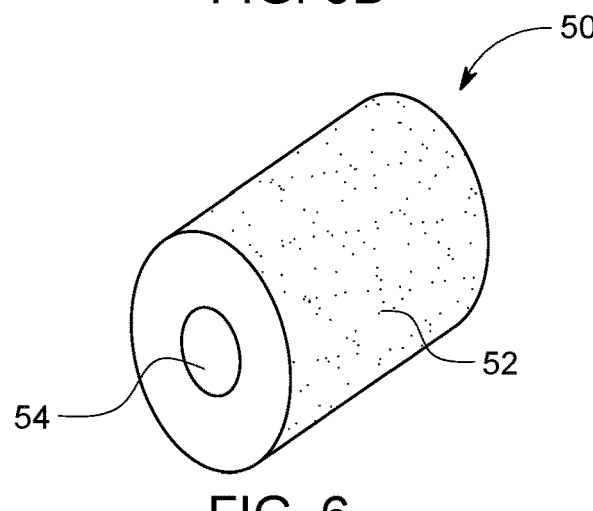
FIG. 6 is a perspective view of a dowel graft for arthrodesis in accordance with the present disclosure.

Turning now to dowel grafts and guides for placing the dowel grafts, FIG. 6 illustrates a typical dowel graft 50 that consists of a cylindrical body 52 having a central bore 54 passing at least partially through a longitudinal axis of the cylindrical body 52.

Figure 7:
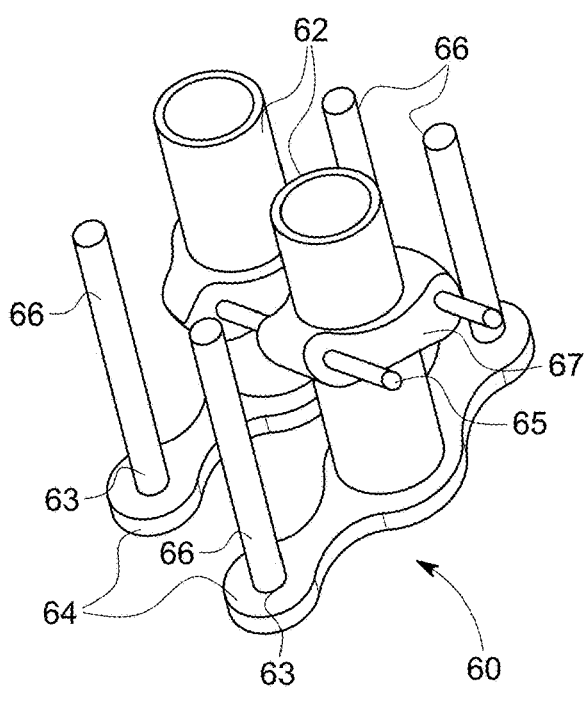
FIG. 7 is a perspective view of a dowel guide in accordance with the present disclosure.
Figure 8:
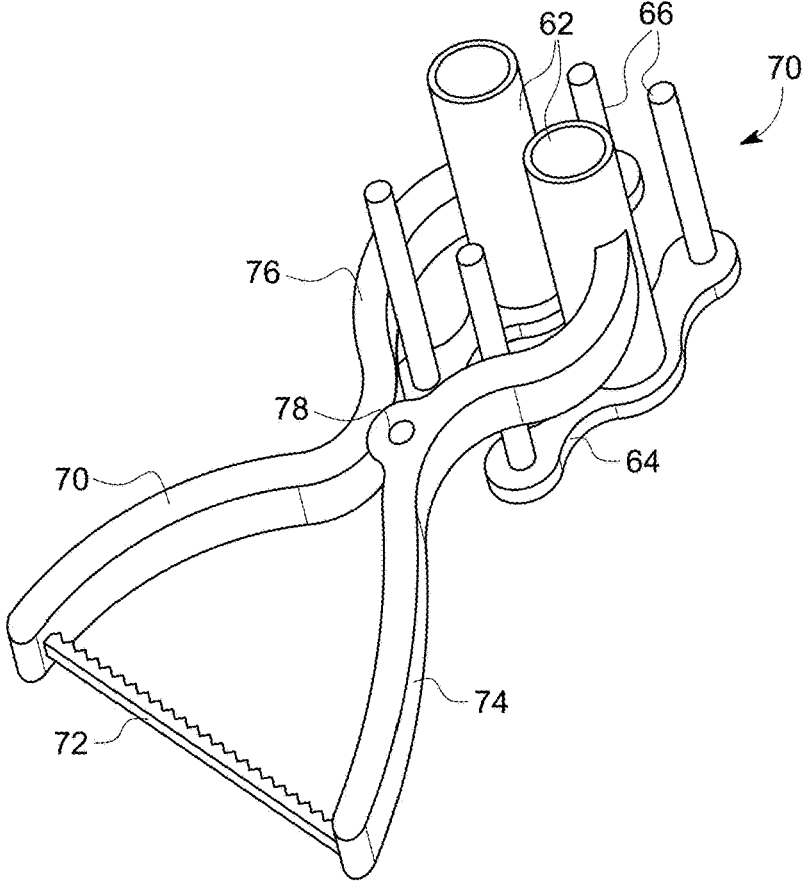
FIG. 8 is a perspective view of the dowel guide of FIG. 7 coupled to a distractor instrument.

FIGS. 7 and 8 illustrate a dowel guide 60 for resecting and placing a dowel bone graft at a fusion site. Dowel guide 60 has at least two barrels 62 laterally adjacent to each other. A first barrel 62 is fixed positionally and, in use, is removably fixated to either the 1$^{st}$ or 2$^{nd}$ TMT joint. A drill or reamer is placed through the first barrel 62, centered on the respective joint and the joint is resected. Once the joint is resected, a bone graft dowel, such as dowel 50 in FIG. 6, described in greater detail hereinafter, is placed through the barrel to graft the fusion site.

A second barrel 62 is movable laterally relative to the first barrel 62. This lateral movability of the second barrel 62 facilitates distraction of the second barrel 62 from the first barrel 62 while the first barrel 62 is removably fixated to either the 1$^{st}$ or 2$^{nd}$ TMT joint such that the second barrel 62 is removably fixated to either the 2$^{nd}$ or 3$^{rd}$ TMT joint, depending upon the position of the first barrel 62. Once the second barrel 62 is removably fixated to either the 2$^{nd}$ or 3$^{rd}$ TMT joint, the first barrel 62 may be removed from either the 1$^{st}$ or 2$^{nd}$ TMT joint post-procedure, and the fusion procedure through the second barrel 156 may be performed on the 2$^{nd}$ or 3$^{rd}$ TMT joint in the manner described above with respect to the first barrel 62.

First and second barrels 62 are tubular with openings at opposing ends of each of the first and second barrels 62. Each of the first and second barrels 62 are mounted on a base plate 64. Base plate 64 has an opening (not shown) communicating with an end opening of barrel 62. Each base plate 64 has wire openings 63 at opposing ends thereof, and each wire opening 63 accommodates a K-wire 66 to pass therethrough, thus, removably fixing and stabilizing the dowel guide 60 across a TMT joint. A retention collar 67 may, optionally, be employed on each of the first and second barrels 62 and each retention collar 67 being coupled to each other to retain the barrels 62 in a desired position relative to one another. The retention collars 67 may be coupled using adjustable members 65 that permit translational movement of the first and second barrels 62 relative to one another. Adjustable members 65 may be threaded members, ratchet members, telescoping members, or other similar members that permit translational movement and positional affixation of the first and second barrels 62 relative to each other.

Alternatively, as shown in FIG. 8, instead of retention collars 67, a distractor instrument 70 may be employed. Distractor instrument 70 consists generally of a pair of handles 74, a pair of jaws 76, and a locking mechanism 72. The jaws 76 interface with the barrels 62 and, under the control of the surgeon using handles 74, translate the first and second barrels 62 laterally relative to one another. The locking mechanism 72, which may be associated with the handles 74 or may be incorporated into a pivot 78 between the handles 74 and the jaws 76 and about which the handles 74 and jaws 76 rotate.

The dowel guide 60 may also have a slot or other opening in the base plates 64 that is configured to permit a compression staple to be placed through the dowel guide 60 to fix the dowel and the bone graft at the fusion site.

Figures 9, 10:
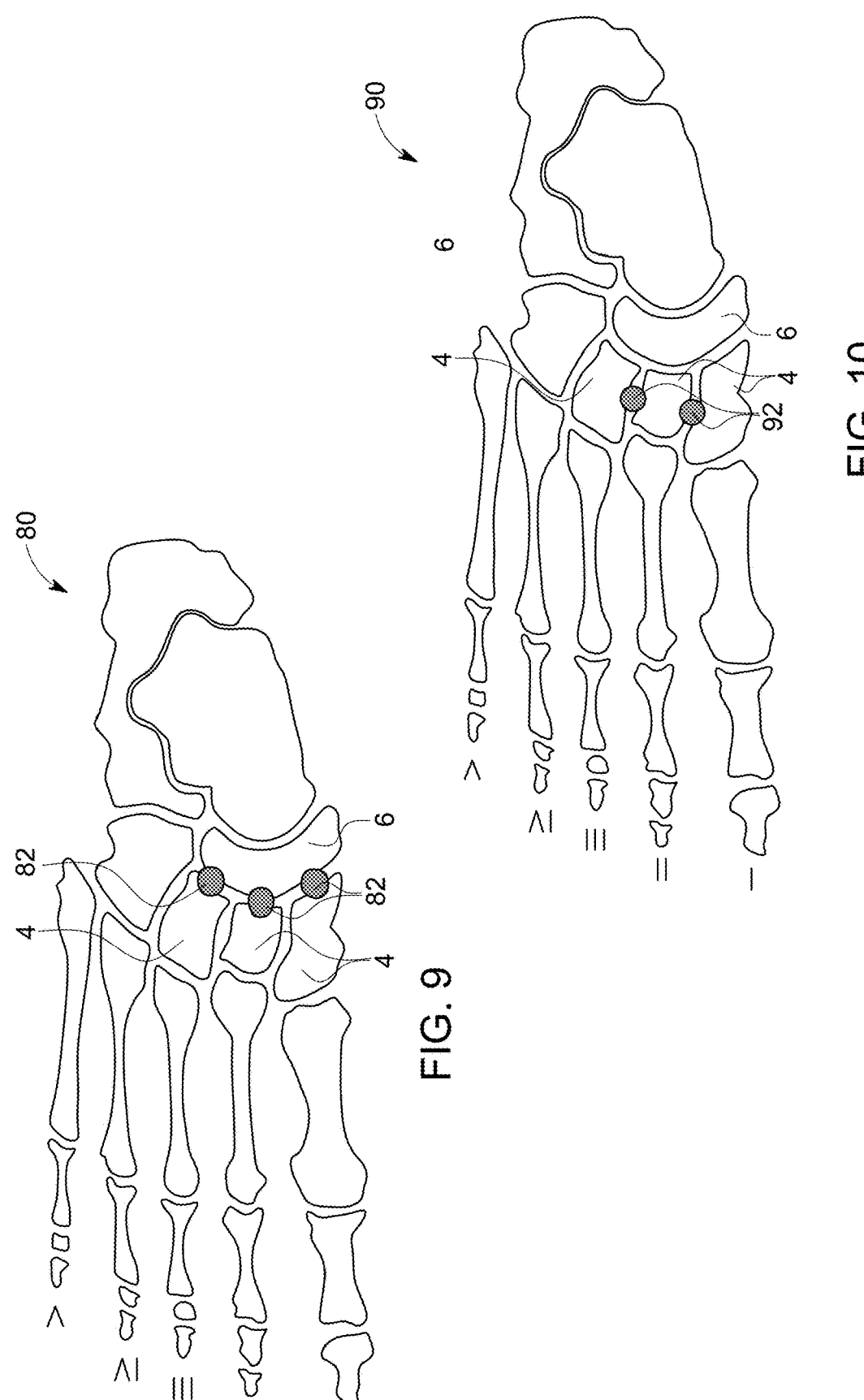
FIG. 9 is a dorsal view illustrating navicular-cuneiform joint fusion positions in the mid-foot architecture for the dowel graft in accordance with the present invention.
FIG. 10 is a dorsal view illustrating intercuneiform joint fusion positions in the mid-foot architecture for the dowel graft in accordance with the present invention.
Figures 11, 12:
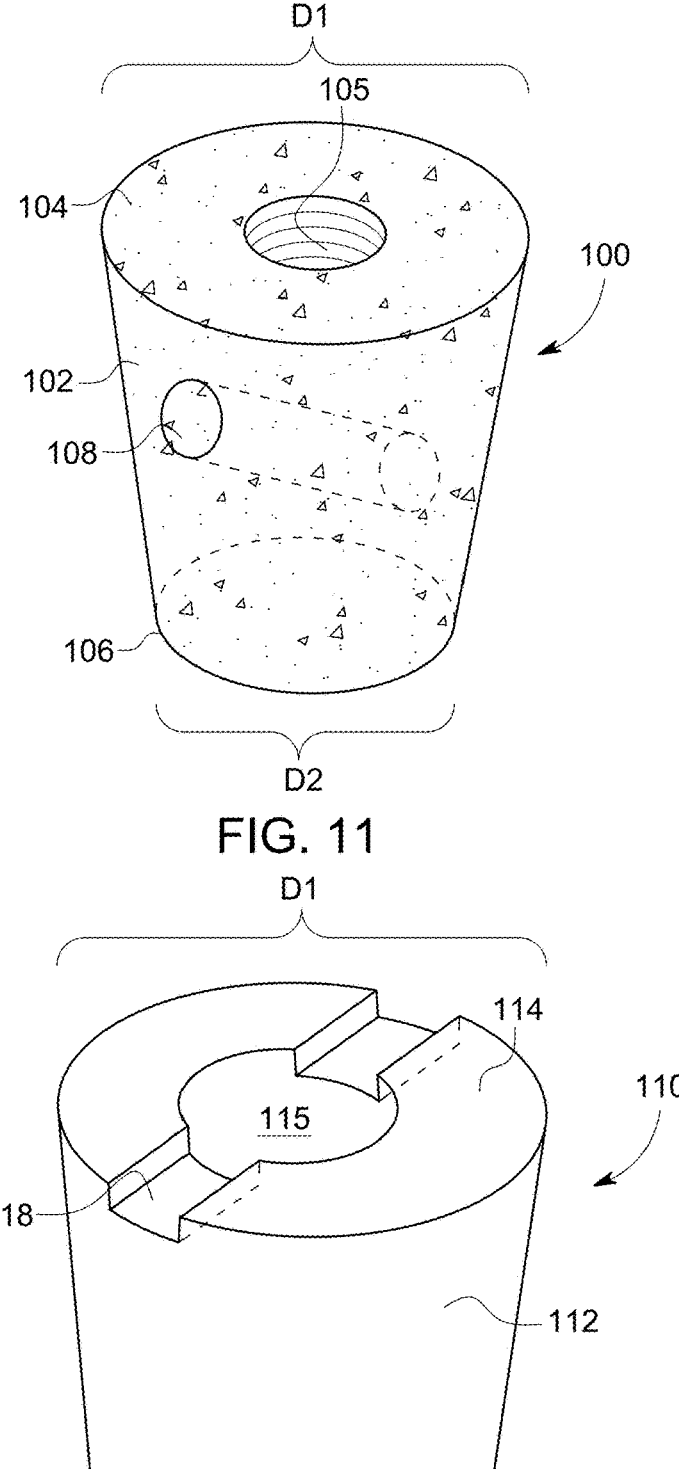
FIG. 11 is a perspective view of a first embodiment of locking dowel fusion device in accordance with the present disclosure.
FIG. 12 is a perspective view of a second embodiment of a locking dowel fusion device in accordance with the present disclosure.

FIG. 9 illustrated anatomical positions for fusion dowel 82 placement for NC joint fusion 80. NC joint fusion is particularly challenging due to the need for joint exposure close location to the tibialis anterior. NC joint fusion fuses the navicular bone 6 with a cuneiform bone 4. The NC joint fusion dowel is preferably made of porous metal and configured either as a mosaic dowel, i.e., a dowel fabricated of multiple component pieces, as a single larger dowel, or as two or more dowels placed into a bore at the NC joint. The dowels may have a cylindrical, trapezoidal, conical, or frustoconical shape.

FIG. 10 illustrates anatomical positions for fusion dowel 92 placement for IC joint fusion 90. IC joint fusion fuses adjacent cuneiform bones of the midfoot. It will be understood that variations in the overall shape of the dowel, the diameters of the proximal and distal surfaces of the dowels, and the wall angles, are specifically contemplated by the present disclosure and included herewith.

Turning now to FIGS. 11 to 16, there are illustrated various embodiments of a dowel fusion system, dowel devices, dowel locking devices, reamer guides for joint preparation, and dowel guides for placement of the dowels.

The dowel fusion system 200 may be employed with TMT joint fusion, intercuneiform fusion, NC fusion, CC joint fusion, and potentially with the carpal bones of the wrist. Central to the dowel fusion system is a dowel 100, 110. Dowel 100, 110 has a frustoconical shape and may be made in variable lengths or depths, variable cone angles, and variable diameters at both its major diameter and its minor diameter, respectively. Dowel 100, 110 may also have different transverse cross-sectional shapes. For example, the transverse cross-sectional shape of dowel 100, 110 may be circular, ovular, elliptical, or polygonal, along an entire or partial longitudinal axis of the dowel 100, 110.

Dowel 100, 110 is preferably made from an osteophilic and porous material having a microstructural pattern similar to cancellous bone. Suitable materials are titanium, polyether ether ketone, or similar biocompatible materials.

In a first embodiment of dowel 100, a proximal attachment opening 105 is provided in a proximal surface 104, with the attachment opening 105 configured to removably couple to an inserter instrument (not shown). Dowel 100 has wall surfaces 102 that taper along a longitudinal axis of the dowel 100 from its major diameter D1 to its smaller minor diameter D2 at a distal end 106 of dowel 100. A transverse bore 108 is formed that passes diametrically through diametrically opposing wall surfaces 102 of the dowel 100 and opens at the opposite wall surface 102. Bore 108 is configured to permit insertion of a locking screw (not shown) into and through the transverse bore 108 and across the joint being fused to opening to limit rotation and migration of the dowel as well as provide compression across the fusion site.

Figures 15, 16:
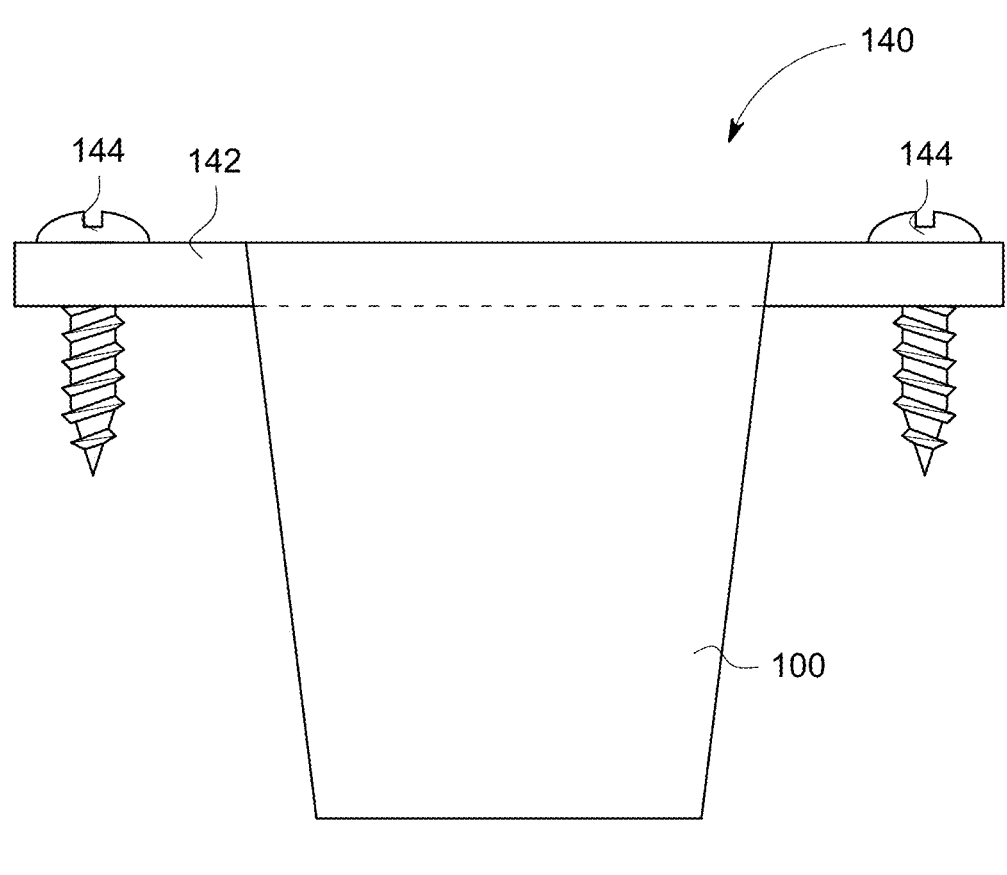
FIG. 15 is a side elevational view of the second embodiment of the locking dowel fusion device showing a compression plate fixation.
FIG. 16 is a side elevational view of the second embodiment of the locking dowel fusion device showing a compression staple.

In a second embodiment of dowel 110, the dowel 110 has a recessed channel 118 in proximal surface 114 that extends entirely across a major diameter D1 of the dowel 110 and intersecting with a proximal attachment opening 115. Like dowel 100, dowel 110 has wall surfaces 112 that taper along a longitudinal axis of the dowel 110 from its major diameter D1 to its smaller minor diameter D2 at a distal end 116 of dowel 110. A compression plate 140, shown in FIG. 15, engages with the recessed channel 118 and projects radially outward from dowel 110. The compression plate 140 has an elongate plate member 142 and may be affixed to the adjoining bones by screws 144. Alternatively, as shown in FIG. 16, the elongate plate member 142 may be a staple 146 having a crown 147 that engages with the recessed channel 118 having legs 148 and teeth that penetrate into the adjoining bones and retain the staple 146 and dowel 110 within the bone.

It will be appreciated that in both of the foregoing embodiments of the dowel 100, 110, the dowel is retained in a fixed position either by a locking screw passing through the transverse bore 108 or by a compression plate 140 or staple 146 engaged with recessed channel 118. Alternative structures or means for locking the dowel 100, 110 in a fixed position are also contemplated by the present disclosure. For example, the dowel 100, 110 may be configured to at least one projection from a tapered lateral wall surfaces 102, 112 of the dowel 100, 110 that engages with the wall of a conical bore in the bone. The conical bore may be made using a conical reamer. Alternatively, the dowel 100, 110 may be configured to have longitudinal or circumferential ribs or other protrusions that frictionally engage the conical bore in the bone. Still further, the dowel 100, 110 may have barbs project from the tapered lateral wall surfaces 102, 112 of the dowel 100, 110 that permit insertion of the dowel 100, 110 into the conical bore, but engage the conical bore to prevent removal of the dowel 100, 110 once it is placed in the conical bore. Yet further, the dowel 100, 110 may be made of a diametrically expandable material that exerts a radial force against the wall surface of the conical bore to make rotation or removal of the dowel 100, 110 difficult. A friction fit interface between bone and the implant may also be used to create fixation.

Figure 13:
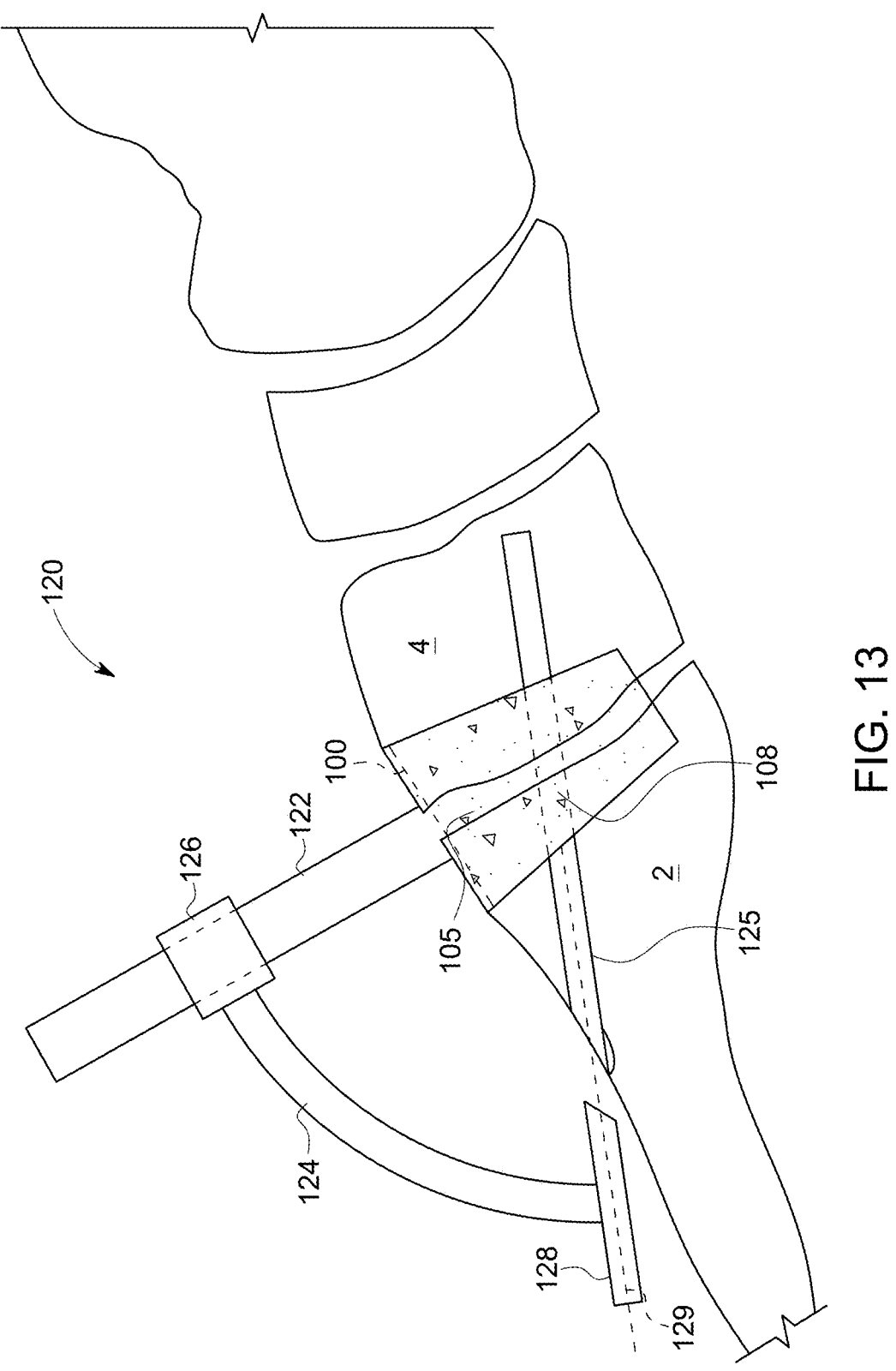
FIG. 13 is side elevational view of a locking screw guide for placement of the first embodiment of the locking dowel fusion device.

To facilitate placement of dowel 100, and as shown in FIG. 13, a dowel guide 120 is placed over the prepared joint to be fused. Dowel guide 120 consists of inserter instrument 122 that couples to the proximal attachment opening 105 in dowel 100. Once the dowel 100 is placed in the reamed recess in, for example, cuneiform bone 4 and metatarsal bone 2, an arm 124 having an engaging collar 126 is coupled to the inserter instrument 122 by engaging collar 126 onto the inserter instrument 122. A drill and screw guide 128 is positioned at an opposite end of arm 124 from engaging collar 126. Guide 128 may consist of a cylindrical member having a central bore 129 in alignment with a sagittal plane of the foot and in alignment with the transverse bore 108 of the dowel 100. This permits a drill (not shown) to pass through the central bore 129 and create a drill bore 125 in both bones across the joint, e.g., in the metatarsal bone 2 and the cuneiform bone 4, and through the transverse bore 108. Once the drill bore 125 is formed, a compression screw (not shown) may be placed into and through the drill bore 125 to compress the adjacent bones across the joint, thereby securing the dowel within the joint being fused. Once the compression screw (not shown) is affixed to the bones and the dowel 100, the inserter instrument 122 and dowel guide 120 are removed and the surgical access closed.

Figure 14:
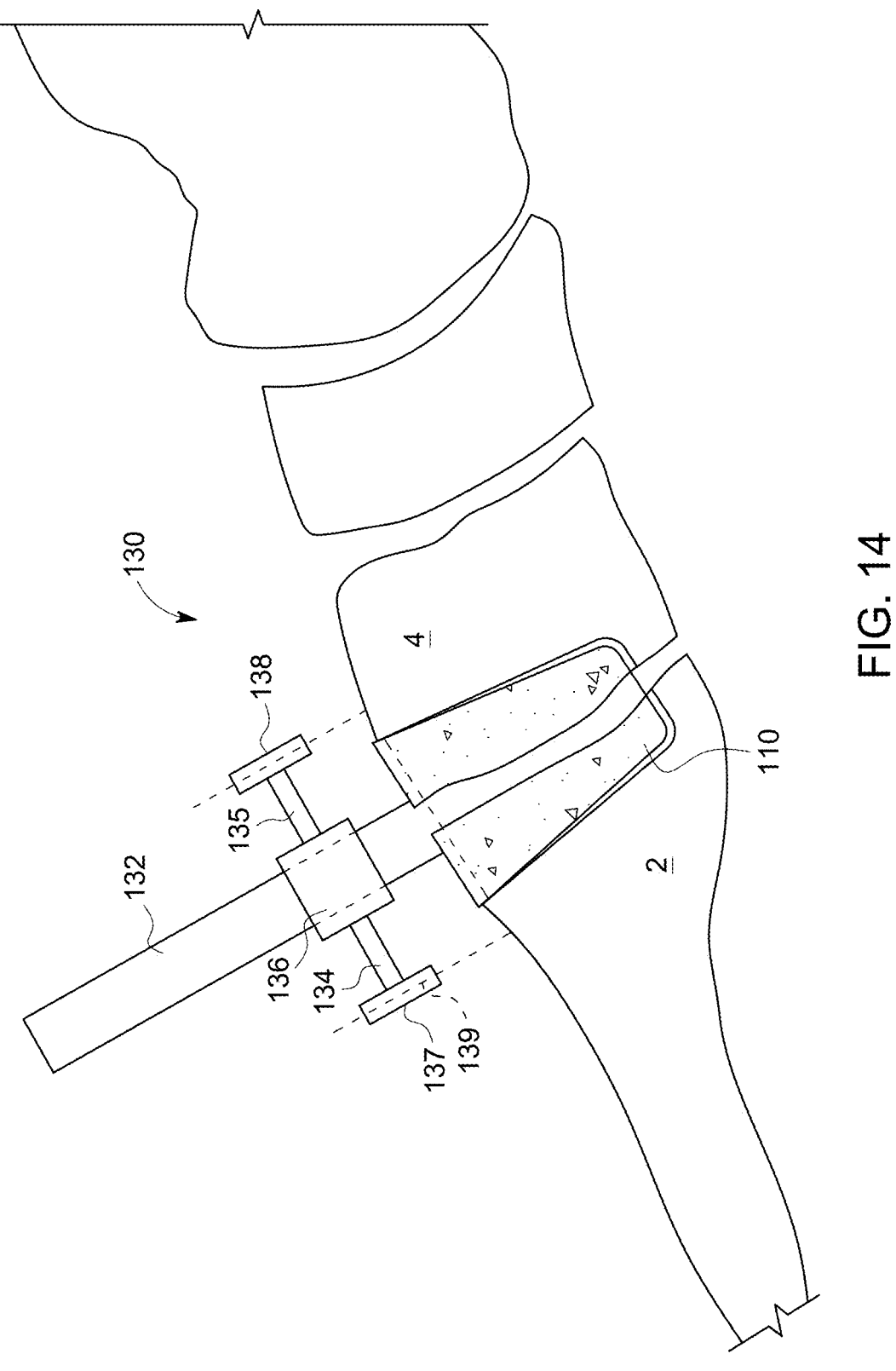
FIG. 14 is a side elevational view of a locking guide for placement of the second embodiment of the locking dowel fusion device.

Placement of dowel 110 is performed by using a second dowel guide 130, as shown in FIG. 14. Dowel guide 130, consists generally of a collar 136 that engages inserter instrument 132 removably coupled to dowel 110 at the proximal attachment opening 115. A pair of radially projecting arms 134, 135 project in opposite directions from each other along the sagittal lane of the foot. Each radially projecting arm 134, 135 has a tubular drill and screw guide 137, 138 affixed to an end thereof. Each drill and screw guide 137, 138 is affixed perpendicularly to its respective radially projecting arm 134, 135, such that a central bore 139 of each drill and screw guide 137, 138 is oriented substantially perpendicular to the dorsal surface of a bone, e.g., metatarsal bone 2 and cuneiform bone 4, on either aspect of the joint being fused. The drill and screw guide 137, 138 permits the surgeon to drill holes into the respective bones to facilitate affixation of compression plate 140 within the recessed channel 118 of dowel 110 and to the bones either by screws 144 or staple 146. Once the compression plate 140 is affixed to the bones, the inserter instrument 132 and dowel guide 130 are removed and the surgical access closed.

According to a method of fusing a joint using dowel 100, 110, the joint to be fused is first freed up by resecting any arthritis or other maladies affecting alignment or articulation of the joint. The bones on each side of the joint are then placed in a desired alignment and the aligned position is temporarily fixated such as with fine wires, e.g., K wires, or clamps. A pilot hole, for example of about 2 mm, is drilled through the center of the joint and a depth gauge is used to measure the maximum joint depth. A guide wire, for example about 2 mm in diameter, is passed into the drilled pilot hole and a conical reamer, with appropriate depth setting given the measured joint depth, is used to drill a conical bore. An appropriately sized dowel 100, 110 is then selected, press fit into the conical bore, and seated flush with the bone surface. Care should be taken not to over-seat the dowel 100, 110 into the conical bore as distraction of the joint will occur. Bone growth stimulant may, optionally, be placed into the conical bore prior to placing the dowel 100, 110 in the conical bore. Once the dowel 100, 110 is seated in the conical bore, the dowel is positionally locked by either the locking screw, compression plate 140, or staple 146, as described above. 23A

A typical correction required for a TMT joint fusion is plantarflexion of the metatarsal bone. In this scenario, the diameter and shape of the reamed recess at the plantar surface of the joint will remain the same. However, on the dorsal surface of the joint, the recess will increase in size in the sagittal plane while remaining constant in the coronal plane. The resulting shape of the recess will be frustoconical with an elliptical profile on both the plantar and dorsal surfaces. The plantar surface will maintain the same width as the reamer and reduce in the sagittal direction while the dorsal surface will have the same width and an increased length in the sagittal direction. One approach to correct for this would be to adjust the joint prior to preparation and fix the position with K-wires. Once completed, the joint would be prepared with the conical reamer and the dowel could be placed. This procedure, however, would not allow for further joint angle adjustment after preparation.

An alternative approach to placing the dowels is to prepare a progression of increasingly elliptical profiles as needed to achieve incremental degrees of plantarflexion from the starting position. The joint would be prepared with a conical reamer in its initial, uncorrected, configuration, after which the correction can be done and the required dowel selected. A set of trial dowels could be provided to allow the surgeon to assess the resulting joint position with each of the various angles of fusion dowels. The benefit of this approach is that the adjustment may be done after the preparation and can be fine-tuned as needed to ensure that the resulting joint configuration will be compatible with the neighboring joints.

The invention claimed is:

1. Mid-foot osteotomy device, comprising a biocompatible implant having a wedge shape configured to be placed between adjacent bones post-osteotomy, the wedge-shaped biocompatible implant has a pre-implant angle and a post-implant angle, the post-implant angle is expandable and configured to provide gradual correction over time post-implant, further comprising an osmotic pump housed within the biocompatible implant.

2. The mid-foot osteotomy device of claim 1, wherein the biocompatible implant is fabricated of shape memory or superelastic material.

3. The mid-foot osteotomy device according to claim 2, wherein the shape memory or superelastic material further comprises a nickel-titanium based alloy.

4. The mid-foot osteotomy device according to claim 2, wherein the shape memory or superelastic material further comprises a polymer.

5. The mid-foot osteotomy device of claim 1, wherein the biocompatible implant further comprises an inflatable balloon.

6. The mid-foot osteotomy device of claim 5, wherein the inflatable balloon is microporous.

7. The mid-foot osteotomy device of claim 5, wherein the inflatable balloon is made of a bioresorbable material.

8. A mid-foot osteotomy device, comprising a wedge-shaped biocompatible implant having a first pre-implant angle and a second post-implant angle, further comprising an osmotic pump housed within the biocompatible implant.

9. The mid-foot osteotomy device of claim 8, wherein the biocompatible implant is fabricated of shape memory or superelastic material.

10. The mid-foot osteotomy device according to claim 9, wherein the shape memory or superelastic material further comprises a nickel-titanium based alloy.

11. The mid-foot osteotomy device according to claim 9, wherein the shape memory or superelastic material further comprises a polymer.

12. The mid-foot osteotomy device of claim 8, wherein the biocompatible implant further comprises an inflatable balloon.

13. The mid-foot osteotomy device of claim 12, wherein the inflatable balloon is microporous.

14. The mid-foot osteotomy device of claim 12, wherein the inflatable balloon is made of a bioresorbable material.

* * * * *